US009669236B2

(12) United States Patent
Raleigh et al.

(10) Patent No.: US 9,669,236 B2
(45) Date of Patent: Jun. 6, 2017

(54) TRACKING OF TUMOR LOCATION FOR TARGETED RADIATION TREATMENT

(71) Applicant: Headwater Partners II LLC, Redwood City, CA (US)

(72) Inventors: Gregory G. Raleigh, Woodside, CA (US); Alireza Raissinia, Monte Sereno, CA (US)

(73) Assignee: Headwater Partners II LLC, Tyler, TX (US)

( * ) Notice: Subject to any disclaimer, the term of this patent is extended or adjusted under 35 U.S.C. 154(b) by 36 days.

(21) Appl. No.: 14/554,959

(22) Filed: Nov. 26, 2014

(65) Prior Publication Data

US 2015/0182760 A1      Jul. 2, 2015

Related U.S. Application Data

(63) Continuation of application No. 13/356,601, filed on Jan. 23, 2012, now Pat. No. 8,900,113.

(Continued)

(51) Int. Cl.
   *A61N 5/10*      (2006.01)

(52) U.S. Cl.
   CPC ......... *A61N 5/1037* (2013.01); *A61N 5/1039* (2013.01); *A61N 5/1049* (2013.01);
   (Continued)

(58) Field of Classification Search
   CPC .. A61N 5/1037; A61N 5/1039; A61N 5/1049; A61N 2005/1051; A61N 5/1067;
   (Continued)

(56) References Cited

U.S. PATENT DOCUMENTS

| 5,207,223 A | 5/1993 | Adler |
| 6,144,875 A | 11/2000 | Schweikard et al. |

(Continued)

OTHER PUBLICATIONS

Sharp, G.C., et al., "Prediction of respiratory tumour motion for real-time image-guided radiotherapy", Phys. Med. Biol., 2004, pp. 425-440, vol. 49.

(Continued)

*Primary Examiner* — Christine H Matthews
*Assistant Examiner* — Joshua D Lannu
(74) *Attorney, Agent, or Firm* — James E. Harris

(57) ABSTRACT

Systems, methods, and apparatuses are provided for targeting diseased tissue with a radiation beam. Functional models can be used to accurately obtain a location of specific tissue using sensors at identifiable locations of the patient's body. Using the relative distances between the identifiable sensor locations can allow a patient to be in various positions. The functional models can be prepared using accurate pre-treatment scans, which can be taken at various body positions (e.g., rotations and/or translations). The trajectory of the beam can be measured efficiently and accurately using beam sensors attached to a beam assembly, where a model maps the beam sensor locations to a trajectory of the beam. Further, a motion model can use measurements made during treatment to obtain a time-dependent functions of the movement of the specific tissue, the change of an optimal beam trajectory over time, or the change in input commands to a beam positioner.

11 Claims, 14 Drawing Sheets

Related U.S. Application Data

(60) Provisional application No. 61/435,195, filed on Jan. 21, 2011.

(52) U.S. Cl.
CPC ......... *A61N 5/1067* (2013.01); *A61N 5/1069* (2013.01); *A61N 5/1077* (2013.01); *A61N 2005/1051* (2013.01); *A61N 2005/1061* (2013.01)

(58) Field of Classification Search
CPC ................ A61N 5/1077; A61N 5/1069; A61N 2005/1061
See application file for complete search history.

(56) References Cited

U.S. PATENT DOCUMENTS

| | | | |
|---|---|---|---|
| 7,352,370 | B2 | 4/2008 | Wang et al. |
| 7,453,983 | B2 | 11/2008 | Schildkraut et al. |
| 7,469,035 | B2 | 12/2008 | Keall et al. |
| 7,515,681 | B2 | 4/2009 | Ebstein |
| 7,567,697 | B2 | 7/2009 | Mostafavi |
| 7,590,219 | B2 | 9/2009 | Maurer, Jr. et al. |
| 7,623,623 | B2 | 11/2009 | Raanes et al. |
| 7,657,301 | B2 | 2/2010 | Mate et al. |
| 7,789,561 | B2 | 9/2010 | Wu et al. |
| 7,792,249 | B2 | 9/2010 | Gertner et al. |
| 7,842,929 | B2 | 11/2010 | Krautim et al. |
| 7,873,403 | B2 | 1/2011 | Lachner et al. |
| 8,121,368 | B2 | 2/2012 | Wiersma et al. |
| 8,130,907 | B2 | 3/2012 | Maurer, Jr. et al. |
| 8,632,448 | B1 | 1/2014 | Schulte et al. |
| 2003/0125622 | A1 | 7/2003 | Schweikard et al. |
| 2004/0116804 | A1 | 6/2004 | Mostafavi |
| 2004/0264640 | A1 | 12/2004 | Myles |
| 2005/0065421 | A1 | 3/2005 | Burckhardt |
| 2005/0096530 | A1 | 5/2005 | Daw et al. |
| 2005/0261570 | A1* | 11/2005 | Mate ................. A61N 5/1049 600/411 |
| 2006/0025669 | A1 | 2/2006 | Ramamurthy et al. |
| 2006/0030768 | A1 | 2/2006 | Ramamurthy et al. |
| 2006/0274061 | A1 | 12/2006 | Wang et al. |
| 2007/0003011 | A1 | 1/2007 | Lane |
| 2007/0071168 | A1 | 3/2007 | Allison et al. |
| 2007/0076846 | A1 | 4/2007 | Ruchala et al. |
| 2007/0078306 | A1 | 4/2007 | Allison et al. |
| 2007/0232897 | A1 | 10/2007 | Horndler et al. |
| 2008/0039713 | A1* | 2/2008 | Thomson ............... A61B 6/037 600/411 |
| 2008/0101665 | A1 | 5/2008 | Collins et al. |
| 2008/0109013 | A1 | 5/2008 | Fu et al. |
| 2008/0130825 | A1 | 6/2008 | Fu et al. |
| 2008/0212273 | A1 | 9/2008 | Bechtolsheim |
| 2008/0212737 | A1 | 9/2008 | D'Souza et al. |
| 2009/0003523 | A1 | 1/2009 | Raanes et al. |
| 2009/0180666 | A1 | 7/2009 | Sheng et al. |
| 2009/0189092 | A1 | 7/2009 | Aoi et al. |
| 2009/0257557 | A1 | 10/2009 | Sumanaweera et al. |
| 2010/0104068 | A1 | 4/2010 | Kilby et al. |
| 2010/0113911 | A1 | 5/2010 | Dempsey |
| 2010/0282983 | A1 | 11/2010 | Wright et al. |
| 2011/0180731 | A1 | 7/2011 | Welsh |
| 2011/0200170 | A1 | 8/2011 | Nord et al. |
| 2011/0211665 | A1 | 9/2011 | Maurer, Jr. et al. |
| 2011/0235860 | A1 | 9/2011 | Keall et al. |

OTHER PUBLICATIONS

Buzurovic, Ivan, "Robotic Tumor Tracking Techniques in Radiation Therapy", Advances in Robotics & Automation, 2012, 7 pages, vol. 1, Issue 1.

Zhang, J. et al., "Development of a geometry-based respiratory motion-simulating patient model for radiation treament dosimetry", Journal of Applied clinical medical physics, Winter 2008, pp. 16-28, vol. 9, No. 1.

Lyatskaya, Y. et al., "Performance and characteristics of an IR localizing system for radiation therapy", Journal of Applied Clinical Medical physics, 2006, 23 pages, vol. 7, No. 2.

Sauer, Otto A., et al., "Methods and tools for navigated radiotherapy", GMS CURAC, 2006, 14 pages, 1: Doc 15.

Raun, D., et al., "Real-time prediction of respiratory motion based on local regression methods", Phys. Med. Biol. 2007, 16 pages, vol. 52.

Depuydt, Tom, et al., "Geometric accuracy of a novel gimbals based radiation therapy tumor", Radiation and Oncology, 2011, pp. 365-372, vol. 98.

Liu, Yaxi, et al., "Delivery of four-dimensional radiotherapy with TrackBeam for moving target using a dual-layer MLC: dynamic phantoms study," Journal of Applied Clinical Medical Physics, 2009, 16 pages, vol. 10, No. 2.

Krauss, A., et al., "The comparative performance of four respiratory motion predictors for real-time tumour tracking," Physics in Medicine and Biology, 2011, pp. 5303-5317, vol. 56.

* cited by examiner

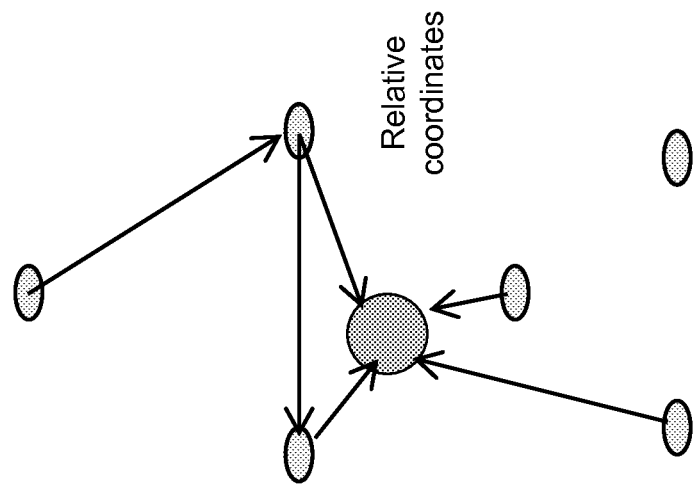
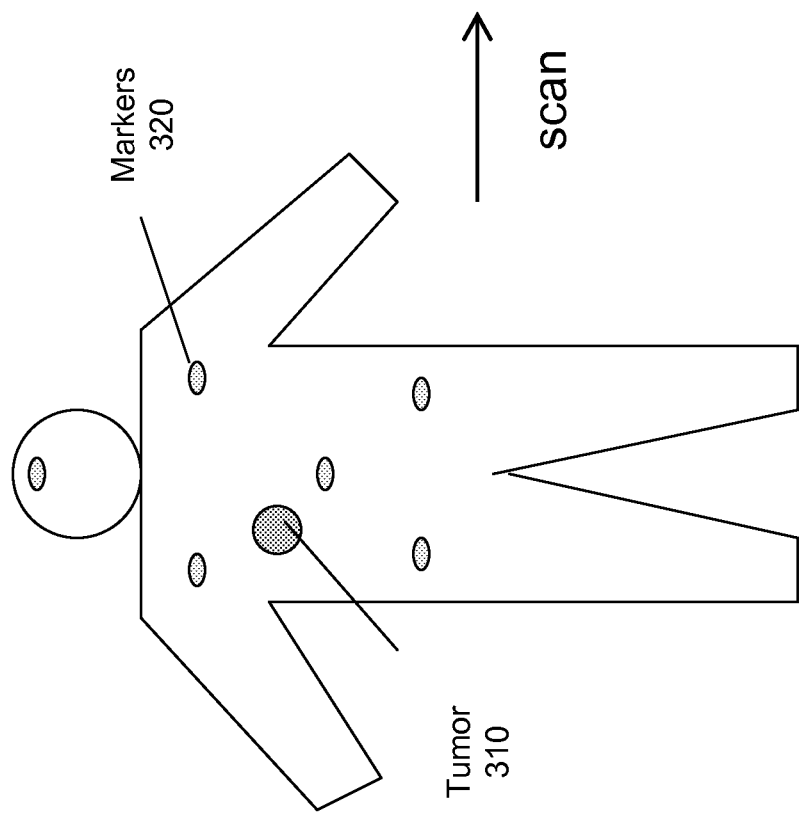
FIG. 3B
FIG. 3A

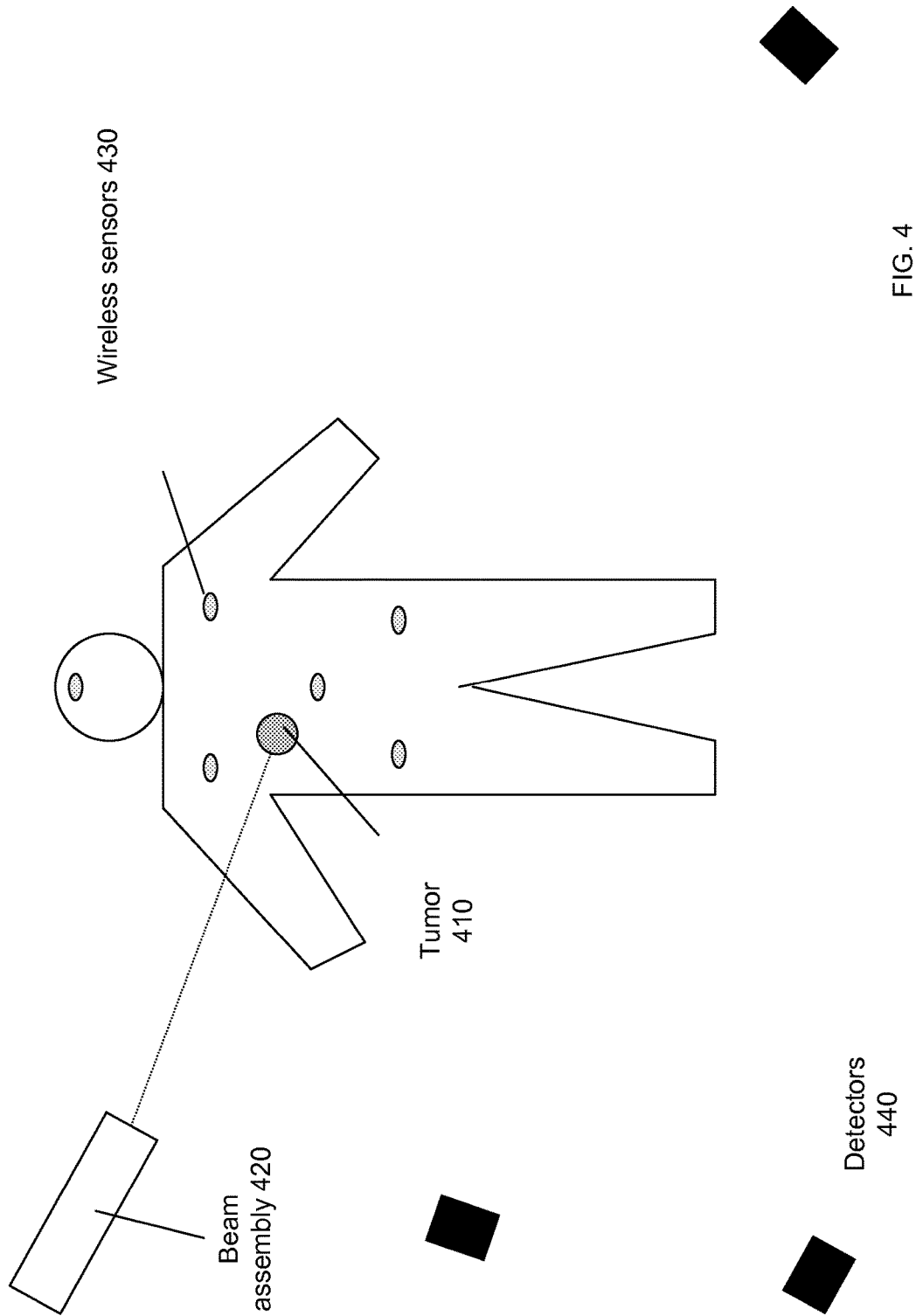

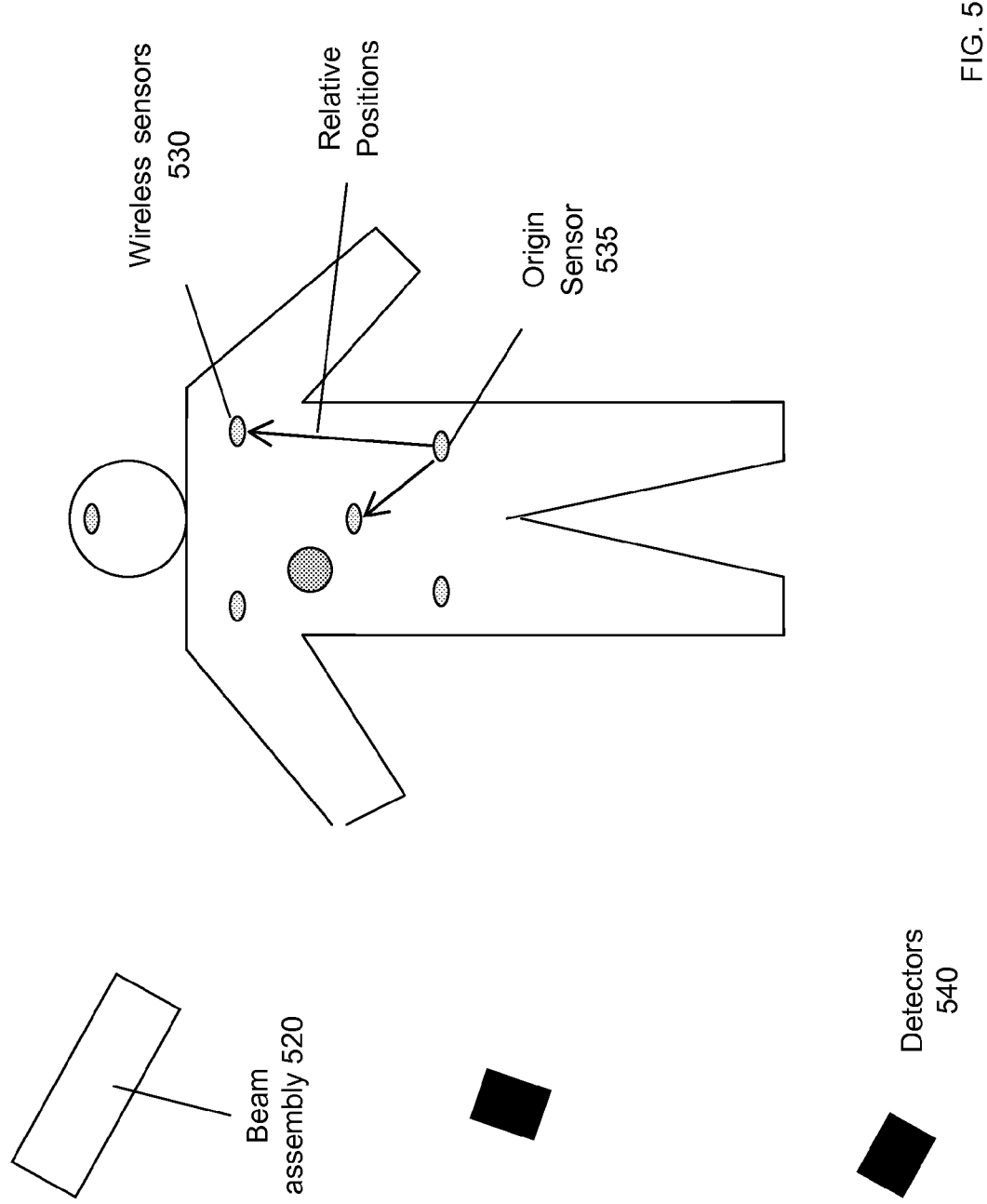

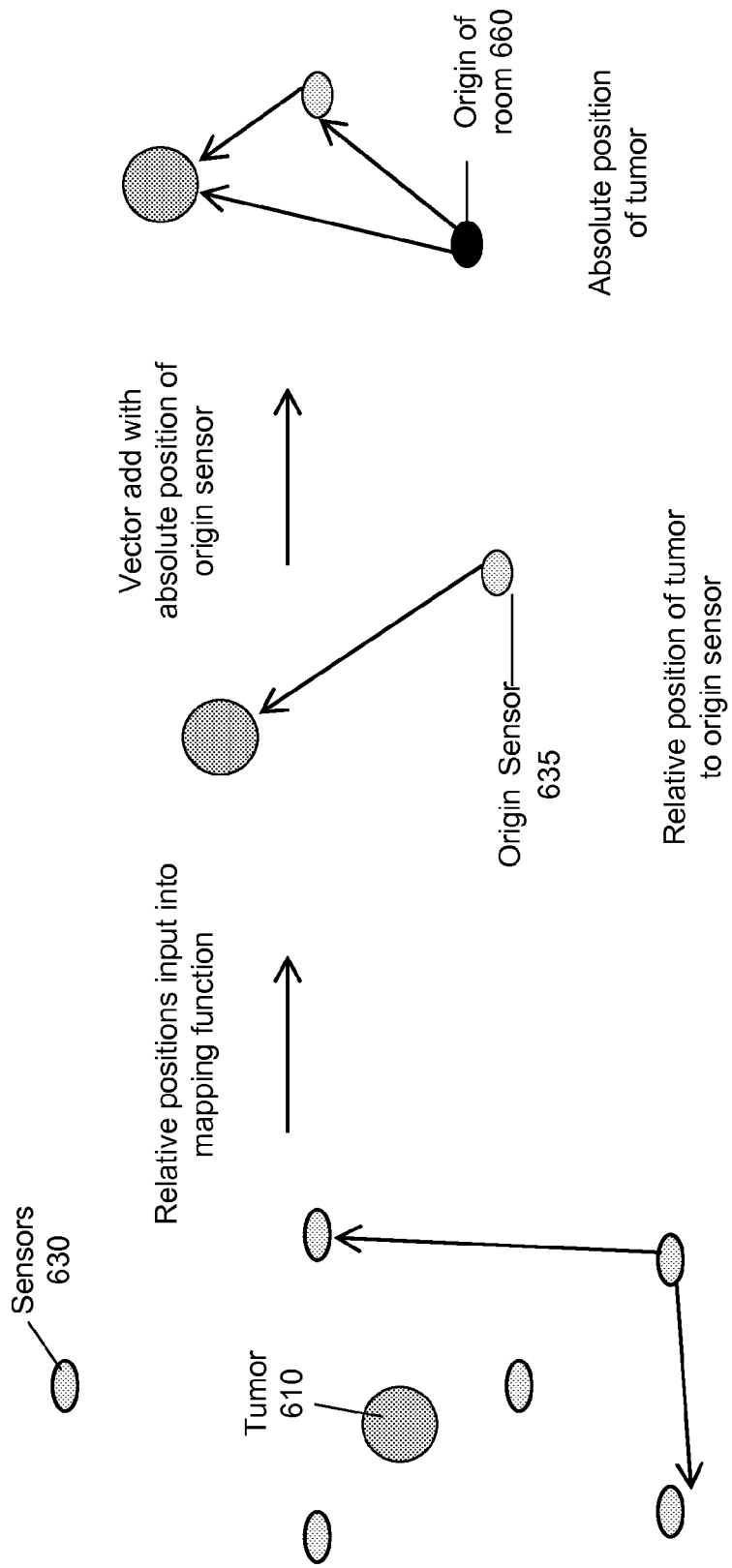

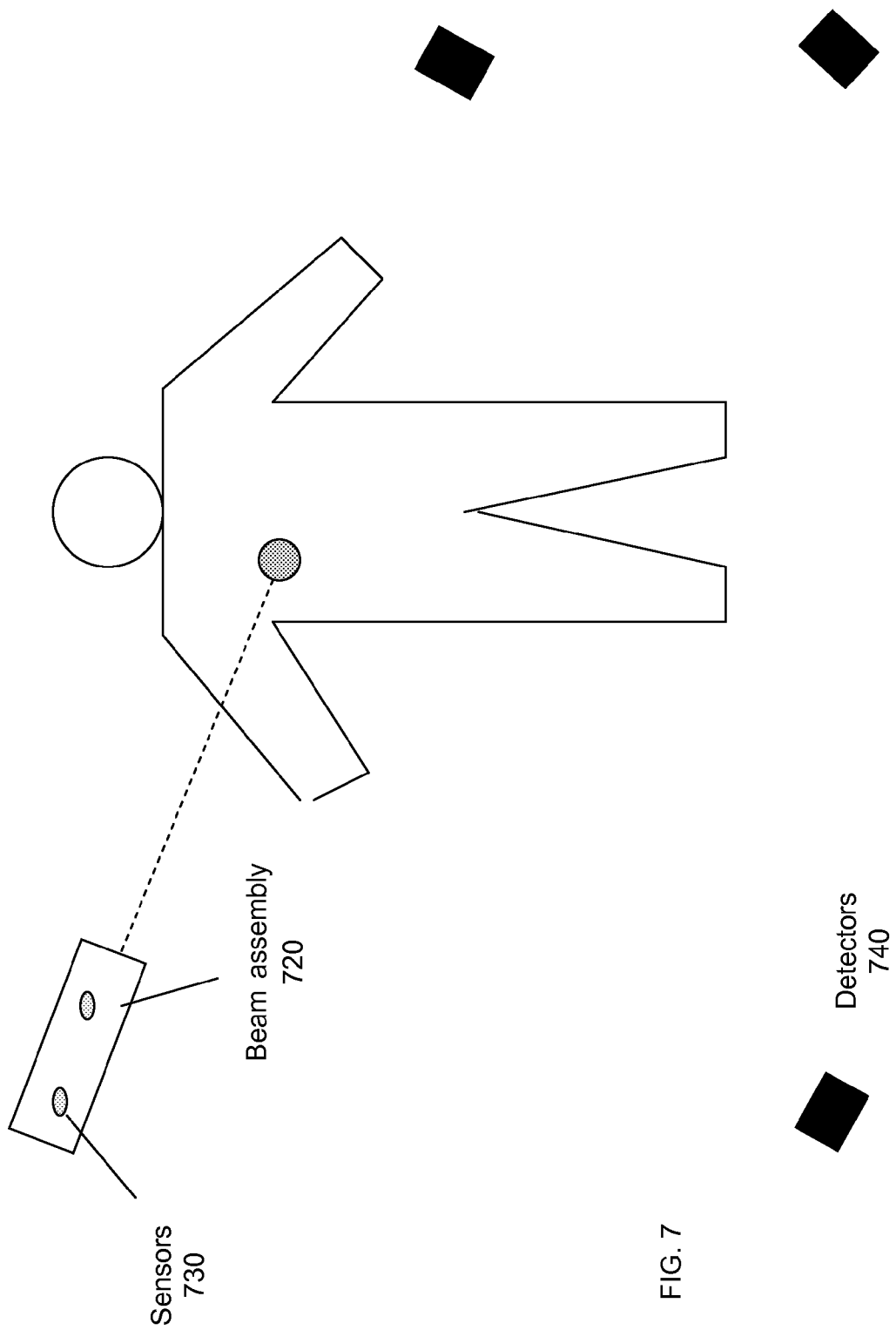

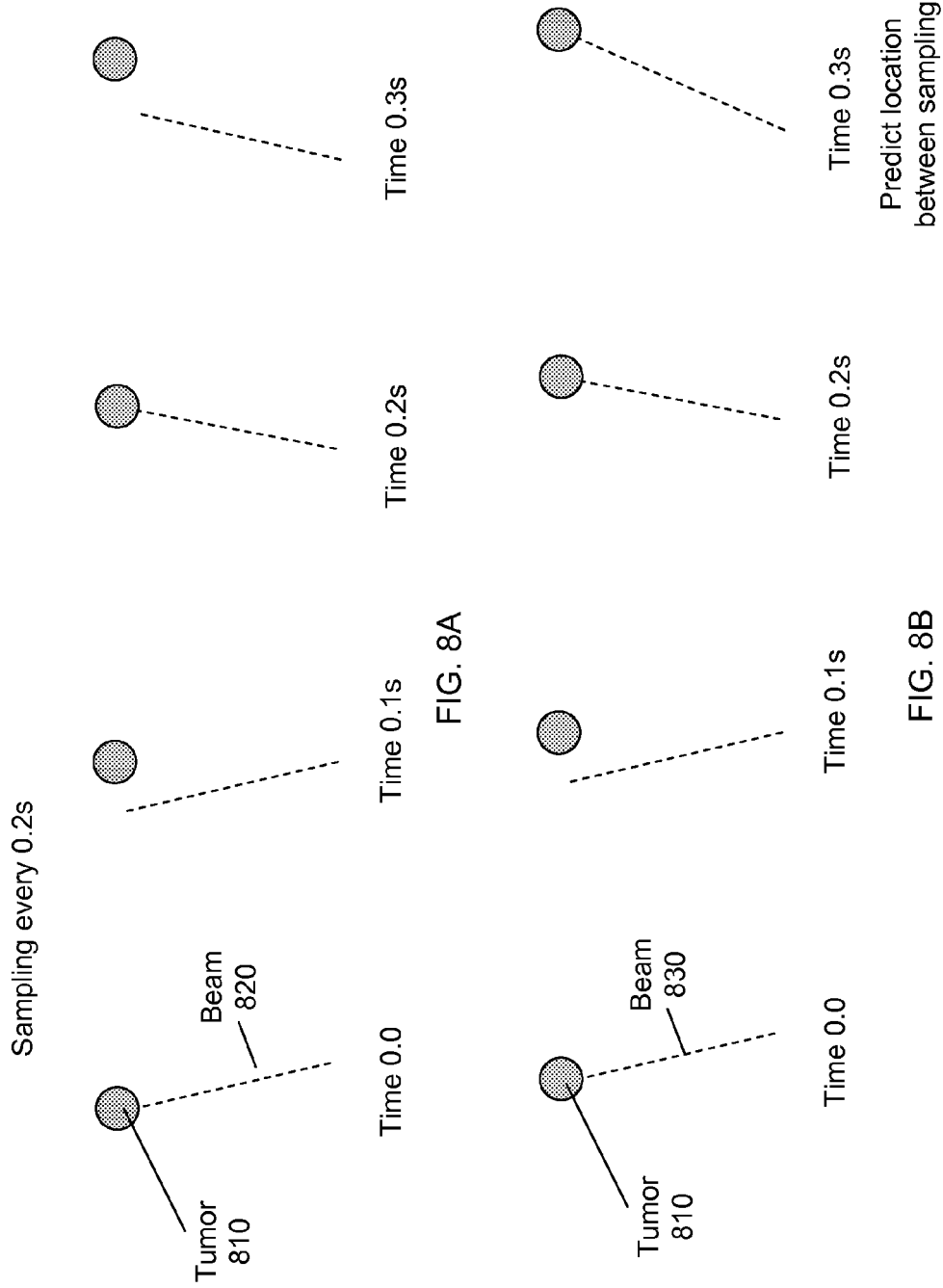

TRACKING OF TUMOR LOCATION FOR TARGETED RADIATION TREATMENT

CROSS-REFERENCES TO RELATED APPLICATIONS

This application is a continuation of U.S. application Ser. No. 13/356,601, entitled "Tracking of Tumor Location for Targeted Radiation Treatment" filed Jan. 23, 2012 which claims priority from U.S. Provisional Application No. 61/435,195, entitled "Non-Invasive Tracking of Tumor Location for Targeted Radiation Treatment" filed Jan. 21, 2011, with both prior applications incorporated by reference herein for all purposes.

BACKGROUND

The present invention relates to targeted radiation treatment (also called radiosurgery), and more specifically to techniques of determining a location of a tumor or other diseased tissue for determining a trajectory of a radiation beam.

Radiation beams have been used to kill diseased tissue (e.g. a tumor). However, the radiation beam can also kill healthy tissue. Thus, methods have been used to determine a location of a tumor so that the radiation beam can be focused on the tumor. For example, the radiation beam can move over time to minimize exposure of healthy tissue while staying focused on the tumor. An x-ray can be taken at the beginning of the treatment to identify fiducials (marking objects) that have been surgically placed on the tumor, thereby providing the location of the tumor. This invasive method is costly and can be dangerous to the patient.

Some methods restrict a patient to a specified position for the duration of a treatment so that the position of the tumor stays known. Such restriction can be quite uncomfortable for the patient, and errors can occur due to imperfect restriction. Methods can take repeated x-rays of internal markers to update the position of the tumor while breathing, but such methods expose the patient to a large amount of radiation via the numerous x-rays and require the motion to be periodic. Methods can omit the implantation of fiducials by correlating a location of certain bones, which tend not to move during treatment, to the tumor location. But, the patient is still restricted to a particular position, or at least a particular orientation (e.g. lying flat on one's back). These methods also still suffer from numerous x-rays if the location of the tumor is to be updated.

U.S. patent publication 2008/0212737 omits the numerous x-rays during treatment and the implantation of fiducials while still accounting for the movement due to breathing; however, the patient is still restricted to certain positions. For example, the patient is restricted to lying on his/her back on a special table while being held in place. A scan is performed at different times during the breathing cycle, with each time in the breathing cycle corresponding to a distance in positions of sensors on the patient's chest compared to a sensor in the special table. The scans can then be used to determine a location of the tumors during radiation beam treatment, but the location is accurate only when the person is in the same exact location as when the scans were taken. Thus, although procedure is non-invasive and limits excessive radiation scans during treatment, the person is still confined and uncomfortable during treatment. Furthermore, this application only handles small periodic motion such as breathing. Different positions of the patient are not allowed.

Additionally, the equipment for creating the radiation beam must be precisely calibrated so that a control input corresponds to the exact location where the tumor is determined to be. The equipment must be made with very high tolerance so that the control inputs correspond the proper beam placement. Thus, the beam equipment can be very expensive. Additionally, current techniques do not properly handle beam positioning error.

Therefore it is desirable to have improved systems and methods for providing targeted radiation treatment that can variously allow a patient freedom of movement without excessive radiation, are easy to use, do not require difficult calibration, are non-invasive, allow movement beyond simply breathing, and compensate for beam positing error and other systematic errors in the system.

BRIEF SUMMARY

Some embodiments can provide freedom of movement to a patient undergoing radiation beam treatment. For example, prior to a treatment session, one or more scans (e.g. MRI or CT) of a patient can be taken to determine a location of a tumor relative to markers of a patient's body. A mapping model can be built from the various relative positions of the markers to obtain an output of the tumor location, which can be done without complicated image reconstruction during treatment. As the markers (sensors) are attached to the patient's body, the patient is not restricted to any particular position or orientation. Thus, scans can be made for different positions of the patient, such as standing up, sitting, and lying down (e.g. on back or side), which can be incorporated in the mapping model. Thus, in one aspect, the patient can choose a natural position specific to that patient. A mapping model can also use scans from other patient's with similar body characteristics to decrease the amount of time and scans to build a model for a patient. Also, a pre-treatment image (e.g., using CT or MRI) can be transformed to a treatment coordinate system, and a best-fit process can be used to map the corrected pre-treatment image onto a treatment image (e.g., obtained from the sensors during treatment). Thus, a patient does not have to be fixed to a specific location.

Other embodiments can provide for accurate determination of the trajectory of a radiation beam, e.g., by obtaining feedback of a beam position using sensors on a beam assembly. In one aspect, a beam assembly using sensor feedback can be less expensive since the control input for positioning of the beam does not need to correspond exactly to the desired trajectory (such precision instruments are expensive and are time consuming to calibrate). For example, the control input can be changed until the sensors indicate that the desired trajectory has been achieved. Such feedback can also provide and maintain greater accuracy relative to instruments that rely on a static relationship between control input and trajectory.

Additionally, embodiments can account for motion of the tissue by creating a time-dependent model based on data taken during treatment. In this manner, the patient can be allowed in other ways besides predetermined types of movement, such as breathing. Additionally, embodiment can address errors in beam positioning. Errors may arise from delays in detecting positions of markers, calculating tumor locations from the marker positions, determining an optimal beam trajectory, and moving the radiation beam to an optimal location. The errors can be handled in various ways. For example, a time offset for computing a next position of tissue can be used to adjust for the delays. Such a time offset can be computed in an open-loop fashion or with a feedback of measured errors. As another example, a model can be used to predict a time-dependent function of the input commands, where the function can be adjusted based on feedback in errors of the actual beam trajectory over time.

Other embodiments are directed to systems, apparatuses, and computer readable media associated with methods described herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers can indicate identical or functionally similar elements.

BRIEF DESCRIPTION OF THE DRAWINGS

FIG. 3A shows a patient 300 with markers 320 according to embodiments of the present invention.

FIG. 3B shows the relative coordinates of markers 320 compared to tumor 310 according to embodiments of the present invention.

FIG. 4 shows a diagram of a patient undergoing treatment according to embodiments of the present invention.

FIG. 5 shows an origin sensor 535 from which the relative positions of the sensors are determined according to embodiments of the present invention.

FIGS. 6A-6C shows the relative coordinates of the sensors being used to determine the location of the tumor location according to embodiments of the present invention.

FIG. 7 shows a system for positioning a trajectory of a radiation beam from a beam assembly 720 according to embodiments of the present invention.

FIG. 8A shows an intermittent error in beam positioning due to movement of a tumor 810 according to embodiments of the present invention. FIG. 8B shows an example of a prediction of a location of a tumor between sampling times according to embodiments of the present invention.

DETAILED DESCRIPTION

I. Introduction

Figure 1A:
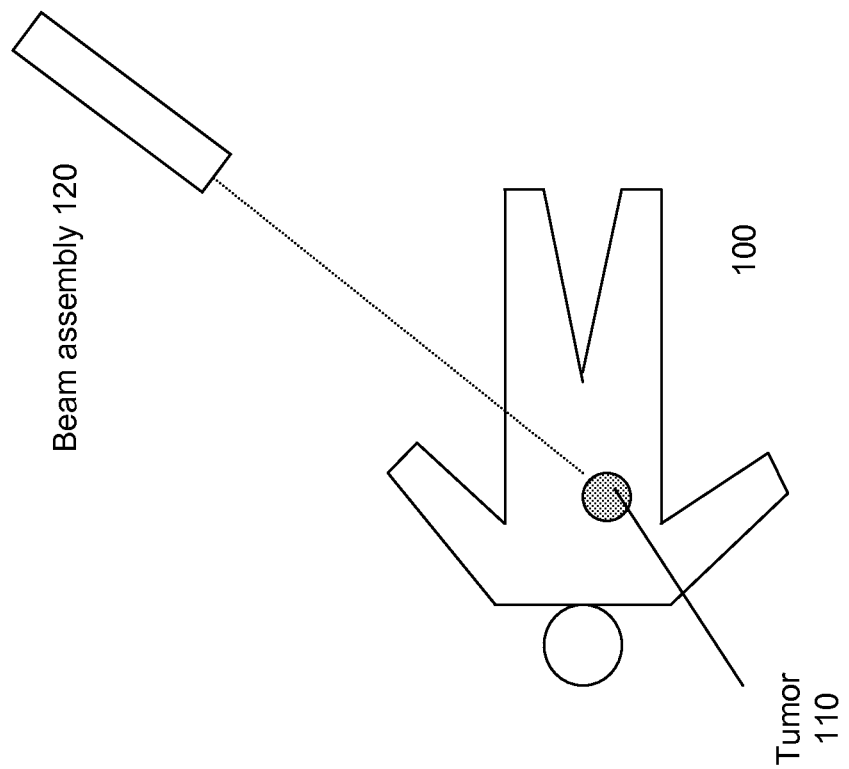
FIG. 1A shows a diagram of a patient 100 undergoing radiation beam treatment according to embodiments of the present invention.

FIG. 1 shows a diagram of a patient 100 undergoing radiation beam treatment according to embodiments of the present invention. The patient 100 is shown as laying down on his/her back, but other body positions and orientations are allowed. A beam assembly 120 is shown in a particular orientation to provide a radiation beam 130 that is focused on a tumor 110 inside patient 100. Beam assembly 120 can be connected to a movement mechanism that allows beam assembly 120 to be moved. For example, beam assembly 120 can be part of a robotic mechanism that sits on a floor of a room, is attached to a wall, or hangs from a ceiling.

In one embodiment, beam assembly 120 may be moved during treatment so that healthy tissue is not irradiated for too long. For example, if the beam always had the same trajectory, the tissue above the tumor 110 would continuously be exposed to radiation. If the beam assembly moved while staying focused, the same healthy tissue would not be continuously exposed.

In order to stay focused on the tumor 110, the location of tumor 110 needs to be known. This is true regardless of whether beam assembly 120 moves during treatment or not. Embodiments can provide non-invasive techniques for determining a location of tumor 110 while allowing a patient to be in different physical positions. For example, some embodiments perform an imaging scan prior to treatment.

Figure 1B:
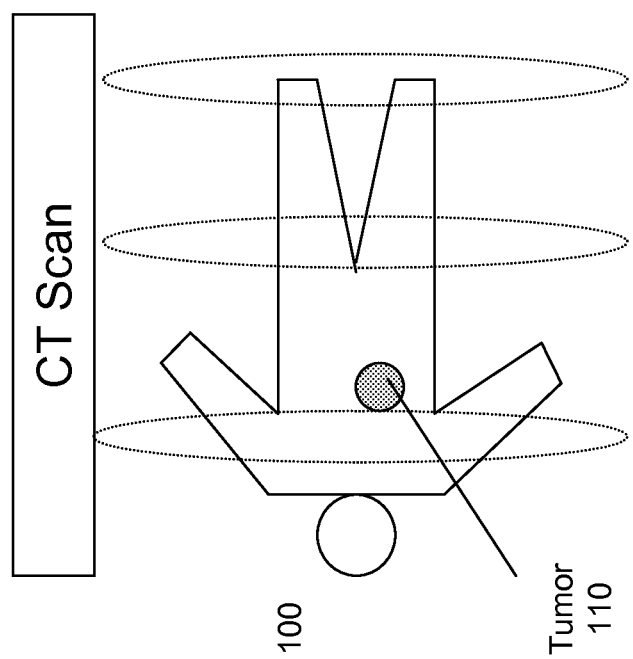
FIG. 1B shows a diagram of a patient 100 undergoing an imaging scan according to embodiments of the present invention.

FIG. 1B shows a diagram of the patient 100 undergoing an imaging scan according to embodiments of the present invention. FIG. 1B is shown on the left of the page to illustrate that this imaging is performed before the treatment. The scan can be in a different room and be done on a different patient visit than the treatment. In another embodiment, the room for scanning can also be used for treatment, and the patient visit can be on the same day. In the embodiment shown, a computed tomography (CT) scan is used, but other suitable scans may be used, such as magnetic resonance imaging (MRI). These accurate scan(s) of the patient and tumor can provide coordinates of the tumor relative to markers attached to the patient's body. Such a method is now described.

II. Using Mapping Model

Figure 2A:
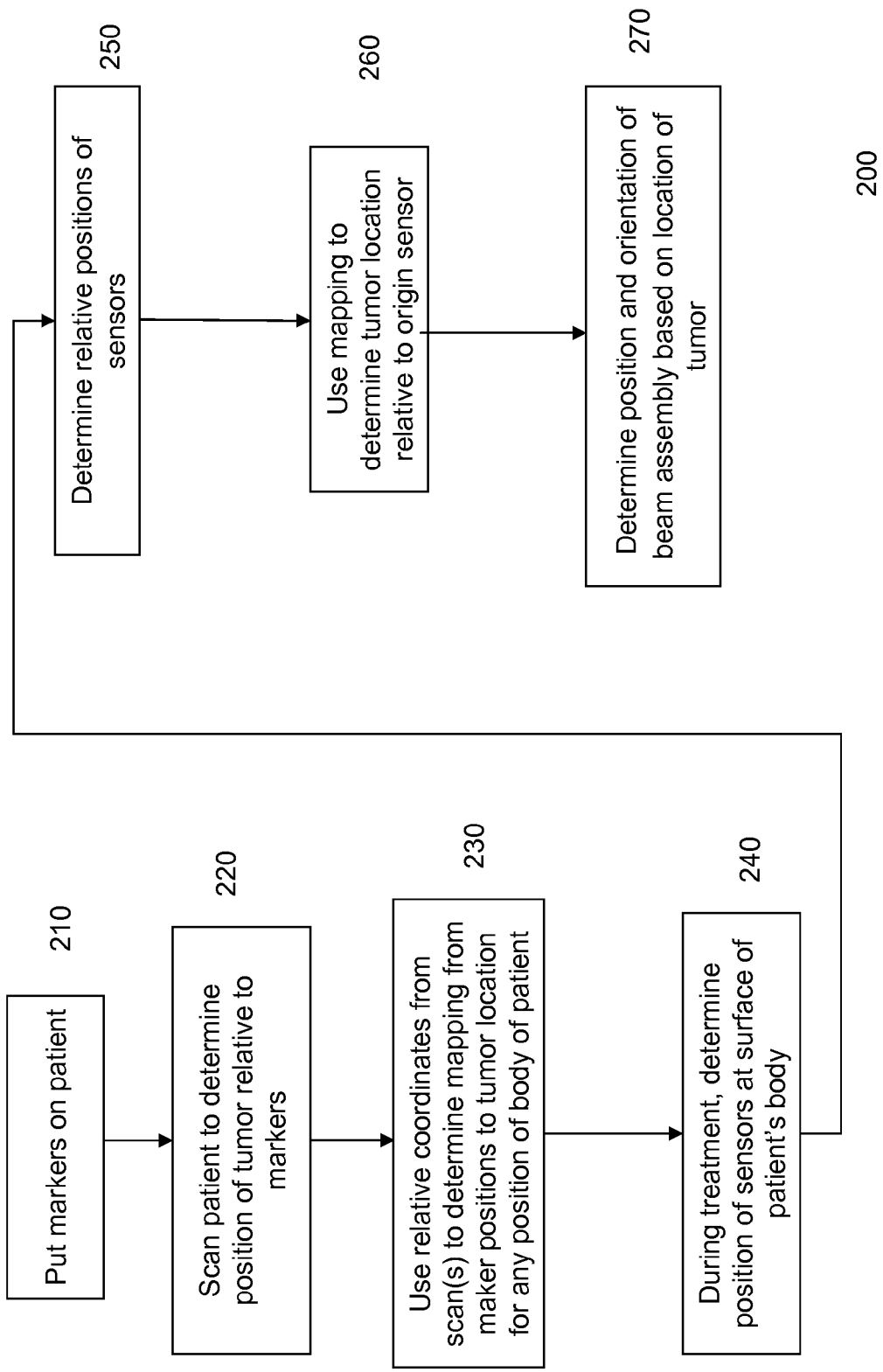
FIG. 2A is a flowchart of a method 200 for determining a location of diseased tissue (e.g. a tumor) according to embodiments of the present invention.

FIG. 2A is a flowchart of a method 200 for determining a location of diseased tissue (e.g. a tumor) according to embodiments of the present invention. In one aspect, method 200 uses imaging scans (such as MRI or CT) to develop a 3D model of the location of the tumor for different physical positions of the patient. The physical positions of the patient can be defined using markers at a surface of the patient's body. Sensors at these marker positions (or at a defined position relative to the marker positions) can be used to determine the physical position of the patient's body during treatment.

In step 210, a plurality of markers are placed at a surface of the patient's body. The markers may be any object (e.g. ink, sensor, pellet, tag, etc.) whose position can be detected during a scan of the patient. In one embodiment, the mechanism for detecting the marker position can be the same mechanism for the scan of the tissue (e.g. MRI), and thus the coordinates of the markers are in the same reference frame as the coordinates of the various tissue that is obtained in the scan. For example, the markers can show up in the image scan. In another embodiment, some other mechanism (e.g. an RF signal or an optical signal) can be used to determine the coordinates of the markers, and the two coordinate systems of the scanned tissue and the markers can be merged such that relative positions between the markers and the various tissues can be determined.

FIG. 3A shows a patient 300 with markers 320 at a surface of the patient's body. The markers 320 can be on the front or back of the patient, head, appendages, or at any other surface of the patient's body. In some embodiments, only one or two markers may be sufficient. In other embodiments, a larger number of markers may be used. The markers can be attached or otherwise put on the patient via any suitable manner, such as adhesives, mechanical attachment to or at a surface of the skin, or just as a layer that binds to the skin. The different makers 320 can be distinguished based on the known locations where the markers were placed, by a unique signature that identifies the marker in a scan, or in any other suitable manner.

The markers can also be identifiable features of a person's body, such as an elbow, a nose (even just the tip), a nipple, belly button, shoulder, etc. The markers can be identified using cameras, such as a typical camera operating with visible light, or other ranges may be used in addition or instead, e.g., infra-red and/or ultraviolet. Thus, artificial markers do not have to be placed on the body, since natural body markers can be used. Natural and artificial markers can be used in combination.

In addition to the identifiable markers on a surface of a body, internal markers could be used, as long as the locations of the markers could be accurately and efficiently identified during treatment. For example, x-rays or ultrasound could detect a position of a particular location on, for example, the spine or femur for the leg, or even soft tissue (which could include the tumor). However, such methods could present difficulties in resolving precise locations of a bone. Such internal markers may provide supplementary information to the positions of the external markers, e.g., in order to refine the mapping model during treatment. For imaging soft tissue during treatment, the accuracy may be low, but some rough values (e.g. located by with larger margins of accuracy than a sensor location) can be obtained. A distance or distance range of the tissue from the sensors (which can be internal markers) can then be compared to the mapping model to ensure that the mapping model is accurate, and to possibly update the mapping model (e.g. using a best fit algorithm). The best fit can determine the maximum likelihood of the tumor location based on the additional scan (i.e. the scan during treatment), which can provide a location of clear internal markers (such as bones), external markers, and a fuzzy location of any one or more soft tissue (which can include the tumor or healthy tissue), along with information from the more accurate pre-treatment scans. In one aspect, the update may be performed when the mapping model is shown to be inaccurate from the best fit model that incorporates In step 220, the patient is scanned to determine the positions of tissue (diseased or healthy) relative to the markers. For example, the absolute positions of the tissue and the markers can be determined in a particular reference frame. Scans can choose any coordinate system (e.g. Euclidean, spherical, etc.) with an arbitrary origin. The absolute coordinates of the tissue and the markers can then be determined in this coordinate system. For example, the coordinates of tumor 310 and of markers 320 can be determined.

In some embodiments, multiple scans can be performed at different body positions, as is described in more detail below. Each scan can provide a different set of relative coordinates. A set of relative coordinates for a particular scan can provide a multi-dimensional point defining a location of tumor 310 for a particular physical position of the patient during a scan. The various physical positions can include sitting upright, laying down, standing, and sitting in a reclined position.

In step 230, the relative coordinates from the one or more scans are used to determine a functional model that maps marker locations to a tumor location for a physical position of the patient. In one embodiment, the functional model receives information for the relative coordinates of the markers as input and provides an output of the location of the tumor. The input locations are not restricted to the relative locations in the one or more scans that were performed, but can be other relative locations that correspond to other physical positions of the patient. For example, intermediate positions may be between laying on a side and laying on a back. The functional model can be created in various ways. In one embodiment, the functional model can have constraints, e.g., some physical positions (relative coordinates) may be rejected if they appear to deviate drastically from normal physical positions (e.g., a rejection of a contortionist body position).

FIG. 3B shows the relative coordinates of markers 320 compared to tumor 310. In various embodiments, the relative coordinates can be to a center of mass of the tumor, center of volume of the tumor, or each to a particular point on a surface of the tumor (e.g. the closest point on the surface relative to a particular marker). The relative coordinates of the markers to each other can be determined from the relative to the tumor, or from the absolute coordinates of the markers themselves.

Figure 3D:
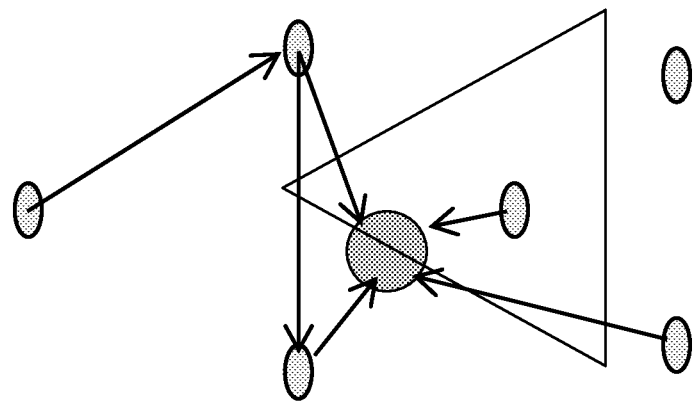
FIGS. 3C and 3D show a reference object 370 that may be used during a scan of a patient according to embodiments of the present invention.
Figure 3C:
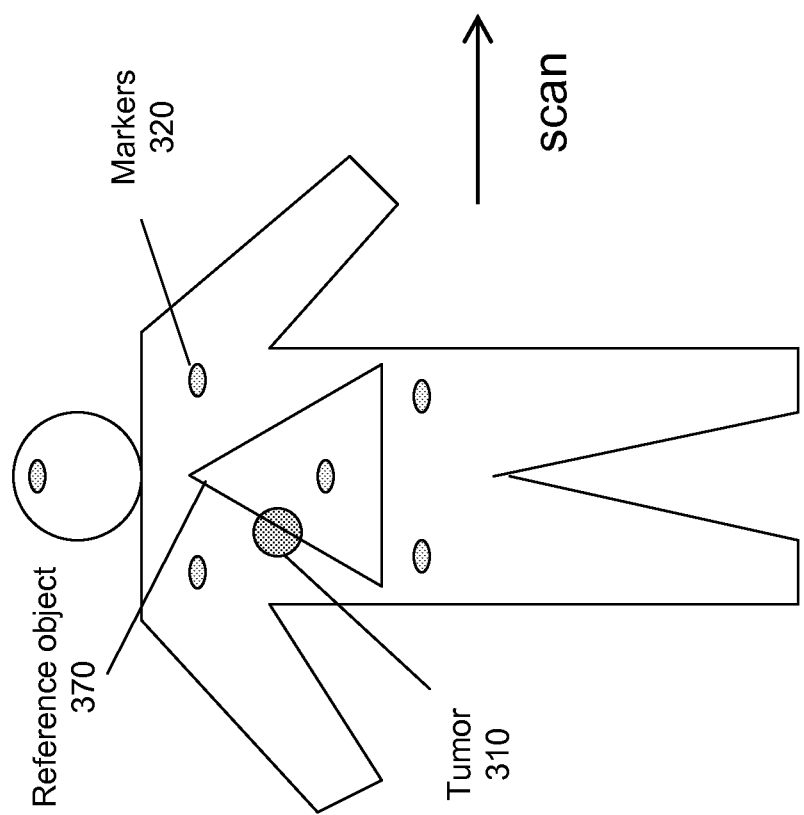

Other objects besides the markers may also be placed at the surface of the patient's body. FIGS. 3C and 3D show a reference object 370 that may be used during a scan of a patient according to embodiments of the present invention. The reference object 370 is shown as a triangle but any shape may be used. The reference object is of a known dimension and its position can be determined in the same manner as the markers. With the known dimension, the distances between the markers can be verified, calibrated, and/or corrected. For example, a length on the image can be obtained from the object, and this length can then be used to obtain the proper scale in the image, which would provide the accurate length between two markers. In one aspect, the relative coordinates would be scaled based on the reference scale provide by the reference object to provide more accurate relative coordinates and relative vectors between the markers.

In other embodiments, a distance of the markers can be measured by hand or some separate mechanism to provide the reference distance. Thus, the reference object could include the markers, e.g., a specific set of markers whose pair-wise distances can be measured. The reference object could also include other marks whose relative distance to the tumor is not used, but whose positions are measured to provide a reference scale for the image. The reference object can be made up of any number of pairs of such marks to provide a reference scale in numerous directions, which can account for variable distortion along different directions.

In some embodiments, more than one reference object may be used. The different reference objects can be used to provide a reference scale in multiple directions. For example, a reference object could be placed on the patients side, thereby providing a reference scale for depth, which can provide corrections that are different than the corrections obtained from a reference object on the patient's torso (which may just provide a reference scale for width and height).

In step 240, sensors are attached to the patient's body and positions of sensors are determined. For example, the sensors can be placed at a surface of the patient's body, or possibly surgically implanted within the patient's body for some embodiments. The positions of the sensors can be determined with respect to a reference point having a known spatial relationship to a radiation beam assembly (e.g. beam assembly 120), which is configured to provide a radiation beam. The sensors may be wireless (e.g. optical, infrared, Wi-Fi, etc.), or be wired. In other embodiments, natural markers (such as facial features, or even bone features, as is described herein) may be used as the sensors, and thus new artificial sensors do not need to be attached.

The position of the sensors can be determined (e.g. sampled) at periodic intervals to track movement of the patient from one position to another position. In one embodiment, the sensors can be at a same location as markers, or simply be the markers. In another embodiment, a sensor can be at a location that is at a predetermined offset from the location of a marker.

In one embodiment, the sensors are placed on a surface of the patient. In another embodiment, the sensors are placed slightly below a surface of the patient's body. Both locations correspond to being at a surface. Similarly, the markers can be placed at a surface of the patient. The sensors can be placed at a same location as the markers. In one implementation, this can be accomplished with a semi-permanent mark (which can be the marker) so that the location of the sensor can be known. The semi-permanent marker can be made to last for the duration of the treatment, which can be anywhere from a day to one week or a month, or longer.

FIG. 4 shows a diagram of a patient undergoing treatment according to embodiments of the present invention. Wireless sensors 430 are at a surface of the patient's body. The positions of the wireless sensors 430 can be determined from detectors 440, which may be connected to a computer system. The wireless sensors can implement any suitable technology, such as zigby, wi-fi, Bluetooth, optical/laser technology etc. For optical sensors, their position can be determined from a reflection of radiation (e.g. visible light) off of the sensor. An optical sensor can even be a particular body feature, e.g., as identified by a recognition algorithm that analyzes a picture of the patient, which may be performed using two or more digital cameras. The pixel positions of the optical sensor on the images from the cameras can be correlated to a particular 3-dimensional spatial coordinate, e.g., using triangulation. The correlation (mapping) may be performed using a best fit algorithm. The mapping can be calibrated with known objects (which may be of known shape) at known distances, e.g., within a treatment enclosure. Such known objects could be flashing or include an active sensor, which may be used to independently confirm or calculate the location of the known object. Thus, the sensor can be the marker used in step 210, including internal markers.

The detectors 440 can be used to triangulate the positions of the sensors relative to an origin of the room. For example, the detectors 440 can each be at a known position, and thus at known positions relative to each other. The signals from each detector can then be compared to determine the position of a sensor. Again, any coordinate system can be chosen, and the origin is arbitrary. In one implementation, the detectors 440 can be calibrated by measuring the relative distances of sensors that have a known spatial relationship.

Embodiments can use various methods to determine the positions of the sensors, such as GPS positioning technology, optical imaging of the sensor locations, and passive or active wireless communication devices. In one embodiment, the sensors could receive signals and then transmit location. In another embodiment, the sensors could transmit signals and detectors can determine the location. In one implementation, the sensors each have a unique signal so that the sensors can be distinguished.

In step 250, positions of the sensors relative to each other are determined from the determined positions of the sensors in the treatment room. In one embodiment, the relative coordinates can be defined with respect to one of the sensors, which can be taken as the origin in the relative coordinate system. Thus, in one embodiment with N sensors in a 3-dimensional environment, N−1 relative positions (each with 3 coordinates) can be determined, where the positions are relative to the origin sensor. In this case, 3*(N−1) relative coordinates would be determined. For example, since there are N−1 sensors besides the origin sensor, there will be N−1 relative positions, and 3*(N−1) relative coordinates.

FIG. 5 shows an origin sensor 535 from which the relative positions of the sensors are determined according to embodiments of the present invention. Note that the relative marker positions can also be measured from an origin marker, and thus the sets of relative positions of sensors can be used as input to the functional model. Beam assembly 520 and detectors 540 can function as described herein.

In step 260, the relative coordinates are input into the mapping model to determine the tumor location. In one embodiment, the tumor location can be defined relative to an origin sensor. A position relative to the origin sensor can then be translated to an absolute position in the treatment enclosure (e.g., the room or smaller containment unit that is meant to house the body), given the location of the origin sensor. For example, the position of the origin sensor can be with respect to a reference point (e.g., an origin of the treatment enclosure). Thus, absolute position can be obtained, where the absolute position is with respect to the reference point.

FIGS. 6A-6C shows the relative coordinates of the sensors being used to determine the location of the tumor according to embodiments of the present invention. FIG. 6A shows the relative coordinates of the sensors 630 at a particular instant in time. The arrows show a vector defining the relative coordinates. Only two relative coordinates are shown, purely for illustration purposes.

The relative coordinates are fed into the mapping function to provide the location of the tumor 610 as defined from the origin sensor. FIG. 6B shows the resulting relative coordinate vector providing the tumor location relative to the origin sensor 635. FIG. 6C shows the position the tumor location relative to an origin 660 of the treatment enclosure (e.g. a room). As shown, the tumor location is obtained as a combination of position of the origin sensor and the relative coordinate of the tumor. Thus, in some embodiments, the tumor location can be determined just from the sensors, and without prior knowledge of the location of the tumor in the room or relative to a stationary object in the room.

In step 270, the position and orientation of the beam assembly is determined based on the location of tumor. The coordinate position and orientation (e.g. angular orientation) of the beam assembly can define the trajectory a radiation beam being emitted from the beam assembly. Since the position of the beam assembly with respect to the reference point is known, and the position of the tumor with respect to the reference point is known, one can determine the position and orientation of the beam assembly that directs the radiation beam to be focused on the tumor. Other factors, such as the location of healthy tissue, can be used to select an optimal position and orientation, such that the beam follows an optimal path. In one embodiment, the wireless sensors (which may be optical sensors) can be used to determine the position and orientation of beam assembly so that the beam stays focused on the tumor, even while the beam assembly is moving so as not to burn healthy tissue.

In one embodiment, locations of healthy tissue are also determined. For example, it may be desired to provide none or minimal radiation to certain organs, e.g., the heart. The locations of these particular organs that can receive none or minimal radiation may be used to determine the proper beam trajectory.

The radiation treatment may be provided in any suitable treatment enclosure, such as a room or a self-contained module. For instance, a capsule (e.g., cylindrical or rectangular) can include the beam assembly and a mechanism to move the beam assembly. For example, the treatment enclosure can have a vertical or horizontal orientation, with the beam assembly being on a support (e.g. a bar) along the long axis. The bar can then rotate around the patient, for example, to provide a cylindrical coverage of the patient. The beam assembly can also have angular degrees of freedom, e.g., the beam can be tilted up and down and side to side. Multiple beam assemblies could be provided on a same support, and there can be multiple supports with different beam assemblies. A small treatment enclosure (particularly if it is self-contained with the beam assembly and detectors, such as cameras or an x-ray device) can facilitate calibration and provide greater accuracy. In one embodiment, the treatment enclosure can also be used in pre-treatment scanning to create the mapping model, or to supplement a previously obtained mapping model.

Figure 2B:
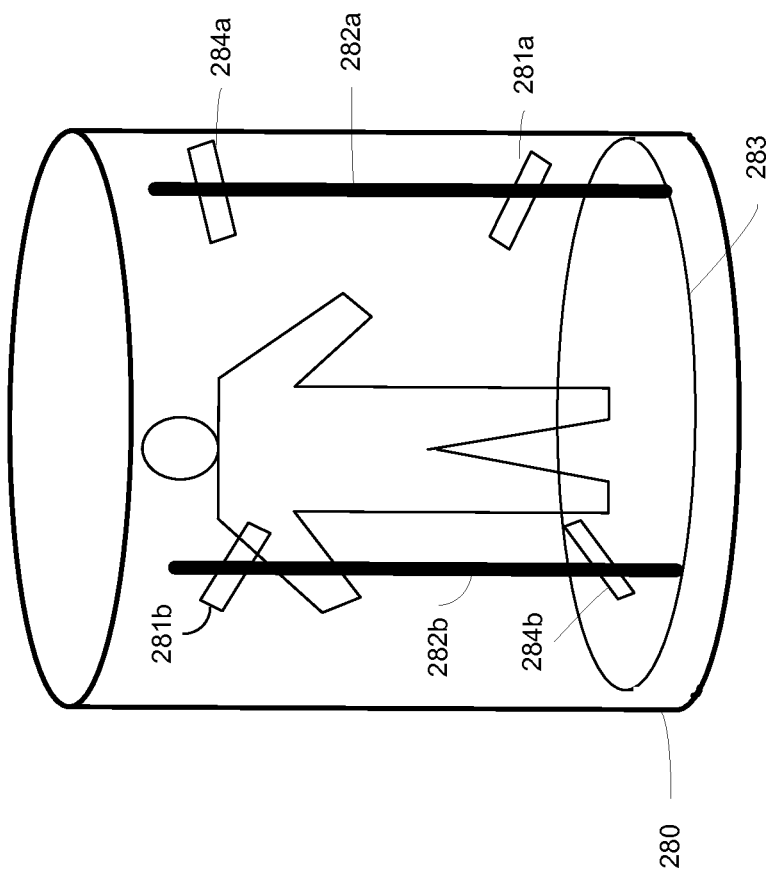
FIG. 2B shows a treatment enclosure 280 according to embodiments of the present invention.

FIG. 2B shows a treatment enclosure 280 according to embodiments of the present invention. The enclosure 280 can be of any shape, and may surround only part of the patient, e.g., just a torso. As shown, the patient is standing, but the patient may be in any position (e.g. leaning against a central object, sitting, or lying down). When lying down, enclosure 280 can have the long axis horizontal. Enclosure 280 can be made with a door for a patient to walk through, or in a horizontal mode a bed can slide in and out from one end of the enclosure. Beam assemblies 281a and 281b can be mounted to supports 282a and 282b. As shown, there are two supports, but other embodiments can have one support or more than two supports. The supports 282 can move on a track 283, which can be near either or both ends of enclosure 280. As shown, track 283 is circular, thereby allowing the supports to rotate. The beam assemblies 281 can rotate, and are shown rotated from horizontal (up and down) and rotated from vertical (left and right). In addition to the beam assemblies, imaging devices 284a and 284b may be attached to supports 282 or to other support structures, such as an inner wall of enclosure 280. These imaging devices can include, for example, x-ray machines, optical cameras (e.g., in the visible and/or infrared spectrum), radio frequency receivers to receive signals from active sensors, or any other suitable imaging device.

III. Using Multiple Scans of Same Patient

As mentioned above, the patient can be scanned prior to treatment, in order to determine a function that maps marker positions to the location of certain tissue (diseased and/or healthy). In some embodiments, multiple scans of the same patient can be used to determine the mapping function.

In one embodiment, each scan corresponds to a different physical position of the body. Each scan can provide the positions of the markers and of the particular tissue (e.g. a tumor). Thus, for N markers, each scan can provide $3*(N+1)$ values, which can be considered as a multi-dimensional data point. An analogy to a simple two dimensional data point $(X,Y)$ as determined by a function $Y=f(x)$ is that the coordinates of the markers are the input values X, and the location of the tumor is the output Y.

In some embodiments, coordinates of the markers can be measured from any origin, e.g. a marker can be considered the origin. Thus, $3*N$ values may define the multi-dimensional data point in the relative coordinate system, with $3*(N-1)$ values for the non-origin markers and 3 for the tumor location relative to the origin marker. In one embodiment, certain markers may be discarded if the dependence of the tumor location on the marker position is flat. For example, a change in the marker position would not affect the tumor location. In this manner, the best or most informative markers can be used.

In one embodiment, the data points can be interpolated, curve fit, etc. to determine a surface that maps the relative coordinates of the markers (e.g. relative to the origin marker) to the relative coordinate of the tumor. In various embodiments, the relative coordinate of the tumor can be defined as a center of mass, center of volume, or other average value related to the tumor.

In another embodiment, the shape of the tumor, as determined from scan(s), can be superimposed onto the tumor coordinate. In one implementation, changes in the shape or orientation of the tumor can also be determined as outputs to a functional model. For example, the orientation can be computed as a separate mapping, as defined by one or more parameters, such as the three Euler angles.

IV. Using One Scan of Current Patient

In some embodiments, only one scan (or just a few) of the patient may be required. The problem becomes how to obtain changes in the tumor location with changes in physical position when only one physical position is obtained. In one embodiment, specific scans or scan information from other patients are used. The functional model can then be obtained using a combination of the one scan for the specific patient and the scan information from one or more other patients, e.g., having similar body shape, height, width and/or body mass. In this manner, the number of scans for a particular patient can be reduced, and the scans from other patients can be re-used, thereby reducing a total number of scans needed, and potentially providing even greater accuracy.

In one embodiment, markers are placed at the same locations for control patient(s). In one embodiment, the location are defined with respect to certain body parts, e.g., at belly button, between eyes, top of spinal cord, etc. As an alternative, body parts that have a fixed relationship to each other can have substituted for placement of a marker. The markers can then be placed at a same location on the current patient.

In one embodiment, the control patients are the same body type as a current patient. For example, control patients of various types may be used, with information from patients with a similar body type being used in combination with the scan of the current patient.

In one implementation, a mapping function can be determined for each control patient. The mappings for different control patients can then be averaged together. In another implementation, the various scans can define data points across patients, and a single mapping can be determined. In one aspect, the data points can be grouped by the patient and then scaled prior to combining to form the single mapping. Accordingly, in one embodiment, a general mapping function is determined from the control patients. If body type (e.g., male, female, overweight, athletic, pear-shaped, muscular, etc.) is accounted for, embodiments can have different mapping function for each body type. Control groups can also be organized by the location of tumor, e.g., which organ has the tumor.

The single scan for the current patient can be used as a scalar on the mapping from the control group. For example, the size of the mapped surface (i.e. a surface that defines the tumor location in the multi-dimensional space for the data points of the scans) can be increased or decreased a certain percentage based on the scalar. Thus, if a person has a same body type but is smaller or larger, a scalar can be used. Different dimensions can have different scalars, e.g., a different scalar for X, Y, and Z, or a different one for R, theta, and phi for spherical coordinates. Thus, a shape of the surface can also be modified. Other transformations besides a simple scalar can also be used.

In one embodiment, a reference object (e.g., reference object 370) can be used in determining how the mapping function from the control group is to be scaled. For example, the reference object can be used to scale the relative coordinates from the one scan, thereby altering the scalar for the control mapping determined from the scan. As another example, the reference object's position relative to features of the patient's body (e.g., eyes, shoulder, etc.) can be used, at least partly, to determine the scaling function to be applies to the control mapping.

In another embodiment, multiple scans can be used to determine how a general mapping function (e.g. as determined from one or more control patients) should be modified for the particular patient. In another embodiment, the few scans can be used to determine a first model, which then is modified based on the more general mapping function, e.g., higher frequency changes of the multi-dimensional surface can be obtained from the general mapping function as more scans may have been used to determine it.

V. Positioning of Beam Assembly

Embodiments can also be used to position the radiation beam. In various aspects, the positioning can be accurate and the beam assembly can be relatively inexpensive compared to current beam assemblies. In one embodiment, such positioning can be achieved using sensors on the beam assembly.

FIG. 7 shows a system for positioning a trajectory of a radiation beam from a beam assembly 720 according to embodiments of the present invention. Sensors 730 are placed on the beam assembly 720. The positions of the sensors can provide a location and an angular orientation of the beam assembly, thereby providing a trajectory of the radiation beam. The detectors can be connected with a computer system that determines the trajectory.

In one embodiment, the sensors are wireless (e.g. optical) and detectors 740 can be used to determine the positions, e.g., by receiving radiation transmitted from or reflected off of the sensors. The sensors can function in a similar manner to any of the embodiments described for the sensors on the patient.

In one embodiment, the system can be calibrated by knowing the exact placement of the sensors on the beam assembly. With such knowledge, the position of the sensors can have a static relationship to the trajectory of the beam. For example, the beam assembly can be built with a certain tolerance that the trajectory will essentially be the same relative to the position and orientation of the beam assembly (which is known from the sensors). The location of the sensors in the room can be calibrated in a separate step, which may be the same step as the calibration for the sensors on the patient.

In another embodiment, the system can be calibrated by detecting the positions of the sensors and then detecting a trajectory of the radiation beam. In one aspect, the beam can be detected at two points to determine the trajectory. The beam can be measured at a particular point in a variety of ways, such as with detectors that are situated on the other side of the patient from the beam assembly. The detectors can have an array of elements having a known position, where the radiation beam activates an element. Some radiation may be absorbed by an element, but some radiation will pass through to activate an element of another detector.

The beam assembly can then be moved to a variety of positions, and the measurement performed again. Each set of sensor positions can define a trajectory, with these values defining a data point for the position of the beam assembly. Therefore, a functional relationship between sensor position and trajectory can be obtained. Not every possible sensor position need to be explored as a functional approximation can provide intermediate values. Also, changes in the trajectory for rotations (e.g. around a single axis) for a particular location can be assumed to provide similar changes in trajectory for the same rotations at a different location of the sensors.

In yet another embodiment, detectors could be used to track the radiation beam during treatment to provide another layer of feedback information. In one aspect, such tracking can happen at a coarser level of refinement, such that the trajectory of the beam is determined by the sensors on the beam assembly more often, but the function of the sensor position to trajectory is updated based on the detection of the beam at larger intervals.

A beam assembly 720 that uses any one or more of the feedback mechanisms can be made cheaper (e.g. expensive stepper motor may not be required) and/or lighter. With these advancements, or even otherwise, two beam assemblies can be used to provide treatment within a shorter period of time. In one aspect, using two or more beams can help to provide a quicker reduction of the diseased tissue than even half the time required for one beam. For example, the amount of heating of the tumor can be greater than double with two beams than just one beam. In another embodiment, each beam can be lower power when used in combination.

In one embodiment, when a location of the tumor is known, a computer can determine a particular trajectory of the radiation beam (e.g., as part of a particular path over time). The beam assembly can be moved and when the desired trajectory is achieved, the radiation beam can be turned on.

VI. Movement of Patient

As mentioned above, embodiments can sample the locations of the sensors on the patient at various intervals during treatment. If the patient moves between samples, then the radiation beam may become unfocused from the tumor (or other diseased tissue), or hit vital healthy tissue. The system can sample the sensor locations quite often in order to minimize such an error. However, if the motion is fast (e.g. relative to the sampling frequency of sensor location) and over a relatively large distance (e.g. as compared to the size of the tumor) so that the motion is not a simple vibration, then errors can persist.

Some embodiments can account for patient movement during treatment, including movement that is relatively fast. Various responses to the movement can depend on the type of movement and can depend on the equipment and functional response of the beam assembly (e.g., the speed at which a beam assembly is positioned). The embodiments described below can be used with embodiments described above (e.g. using relative coordinates) as well as other techniques, e.g., where sensors are attached to the tumor itself.

A. Predicting Location Between Samples of Position

FIG. 8A shows an intermittent error in beam positioning due to movement of a tumor 810 according to embodiments of the present invention. At time 0 seconds, the beam 820 is focused on the tumor 810. The sampling frequency of the sensors is 0.2 seconds. At time 0.1 s, the tumor 810 has moved (e.g., due to the patient moving), and the beam 820 is no longer focused on the tumor. If the movement was small, then the beam might simply be focused on an edge of the tumor. But, as shown, the movement was relatively fast, and thus the beam is no longer focused on the tumor. Such an example may be an extreme example, but is used to better illustrate embodiments of the present invention.

At time 0.2 s, the beam 820 is again focused on the tumor 810. Given that the sensors were sampled at 0.2 s, the location of the tumor was deduced, for example, from the relative coordinates of the sensors using a model as described in any of the embodiments described herein. This example assumes that the beam was focused instantly when the sensor locations were read; however, a delay can occur, which embodiments can also account for, as is described below. At time 0.3 s, the tumor 810 again has moved (e.g., with approximately a constant velocity or acceleration), and thus the beam 820 is again not focused on the tumor 810.

Some embodiments can identify that motion is occurring, and use information about the motion to focus the beam in between sampling of sensor locations (and thus between times when the tumor location is known). Such embodiments can predict where the tumor will be, and thus predict a particular trajectory of the tumor between samples. For example, the position of the tumor at several times can be used to calculate an acceleration and or time. Thus, for linear motion, the equation (position (x)=0.5*acceleration*time$^2$+velocity*time+initial position) can be used to predict where the tumor location will be at any time between the sampling times. In one embodiment, the values of acceleration, velocity and initial position can be considered three dimensional vector parameters for the equation of motion. The variables of acceleration and velocity can be computed using simple algorithms (e.g. using two data points for velocity or three for acceleration), or many data points, which can involve optimization of a cost function. Other functional forms for law of motion can include simple harmonic motion, which may be linear or circular.

Besides models that are based on laws of motion, time-dependent functions for predicting the a next location of the tissue at a future time period can have other functional forms. For example, Fourier functions (such as sine and cosine) Legendre polynomials, spherical harmonics, or any other basis functions can be used to approximate the data points obtained from measuring the location of the tissue over time. The variables (e.g. linear coefficients) can be determined via an optimization algorithm that minimizes a cost function, e.g., a difference in the time-dependent function and the measured locations of the tissue, a difference in the variables from one optimization (e.g. at a first time) to another optimization (e.g., at a later time). The other time-dependent functions can be implemented in a same way as the laws of motion to determine where the beam should be pointing between samples or at a point in time that is later than the time of a position measurement. As each new data point of the measured location of the tissue is obtained, the time-dependent functions can be updated through a new optimization of the cost function, which has changed due to the new data point.

FIG. 8B shows an example of a prediction of a location of a tumor between sampling times according to embodiments of the present invention. In FIG. 8B, the location of the beam 830 is the same as beam 820 at times 0 seconds, 0.1 seconds and 0.2 seconds. Given that there is data for three sampling times, a velocity and acceleration of the tumor can be determined. This acceleration and velocity can be used to move the beam 830 to be focused on the tumor 810 at time 0.3 seconds, and potentially any time between 0.2 seconds and 0.3 seconds. Thus, the update of the beam position can be more often than the sampling frequency of the sensors.

In one embodiment, a minimum number of sampling locations can be required before the movement of the tumor is predicted, and the predicted location used to position the beam between sampling times. Such a requirement can ensure that the equations of motion are accurate and that the motion of the patient is consistent enough to determine a predictive equation.

In other embodiments, other equations of motion can be used. For example, circular motion could be detected, or other curvilinear motion. In one embodiment, a computer system can have a predetermined number of equations for various types of motion. Each type of motion can be associated with a particular equation. Once the location information is matched to a type of motion (e.g. linear, curvilinear, rotational) then the corresponding equation can be chosen and parameters of the corresponding equation chosen. Other types of motion, such as periodic, can provide combinations to determined the equation. For example, a particular equations can exist for periodic linear motion and a different equation for regular linear motion. In some implementations, one type of motion can be initially identified, and subsequently, a new type of motion can be identified (e.g., linear first and then periodic linear subsequently). In one implementation, the parameters for each possible equation can be calculated at each sampling time, and a type of motion can be determined for that sampling time, with the corresponding equation being used to predict the tumor location until the next sampling time. In another implementation, the decision of which type of motion and which equations of motion to use can be performed at every Nth sampling time, where N is greater than one. The determination for which equation (model) is to be used can be determined by comparing a best fit of the parameters of each model to the location information and selecting the model that provides the best fit. The best fit can be determined by calculating an error for each model, e.g., an error between the model and the determined locations of the diseased tissue.

B. Predicting Location with Delay in Beam Positioning

A delay can exist between the time that the locations of the sensors are determined and the time that a new tumor location is determined from coordinates of the sensors (e.g. relative coordinates of the sensors). There can also be a delay between the time that the new tumor location is provided to a beam positioning mechanism and the time that the beam is positioned at the input tumor location. After these delays, the tumor may have already moved to a new location. For example, in FIG. 8A or 8B after a sampling at 0.2 s, the beam may not be re-positioned until 0.21 seconds, and thus the tumor would have moved to a new location based on a particular acceleration and velocity during the intervening 0.01 seconds. In addition, any healthy tissue, which is sought to be avoided, can also have moved thereby causing the beam to hit vital healthy tissue (e.g. the heart). Such a problem could be even worse if these delays are greater than the sampling frequency.

Some embodiments can reduce a beam positioning error due to a time lag between the time a set of position samples are electronically measured and the time required to (i) record the measurements, (ii) process the measurements, (iii) use the measurements to calculate where the beam should ideally point, and then (iv) cause the beam assembly to move to the new pointing position. By knowing how long the lag is for this sequence of measurement, processing and positioning steps, the beam can be positioned according to an estimate of where the beam should ideally be positioned at the end of the time lag, rather than using an estimate of where the beam would have been ideally positioned at the time the measurements were sampled (at the beginning of the time lag) under the assumption the tumor (and possibly the undesired tissue) are stationary.

Figure 9A:
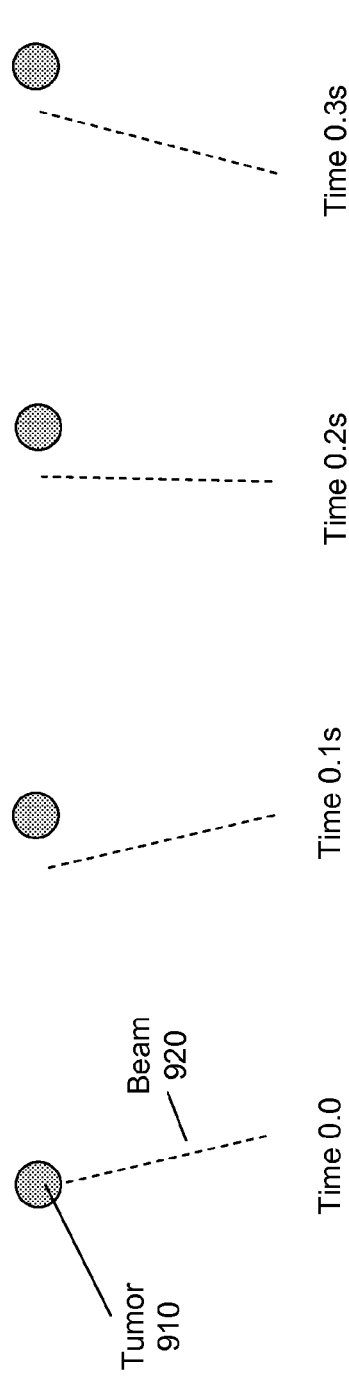
FIG. 9A shows a constant error in beam positioning due to movement of a tumor 910 according to embodiments of the present invention.

FIG. 9A shows a constant error in beam positioning due to movement of a tumor 910 according to embodiments of the present invention. In this example, the sampling frequency is 0.1 seconds, but there is a delay of 0.1 seconds from the time the sensor location are detected and the re-positioning of the beam. At time 0.0, the beam 920 is focused on the tumor 910 (e.g. because the tumor 910 has been stationary). From time 0.0 to 0.1 seconds, the tumor 910 moves and the new sensor locations are detected. However, the beam 920 has not been re-positioned yet, so there is an error.

At time 0.2 seconds, the beam is updated to have the position of where the tumor 910 was at time 0.1 s, but now the tumor 910 has moved to a new position. Thus, there is still an error. Accordingly, the positioning may always lag behind the actual tumor location if the tumor continues to move faster than the system can re-position.

Figure 9B:
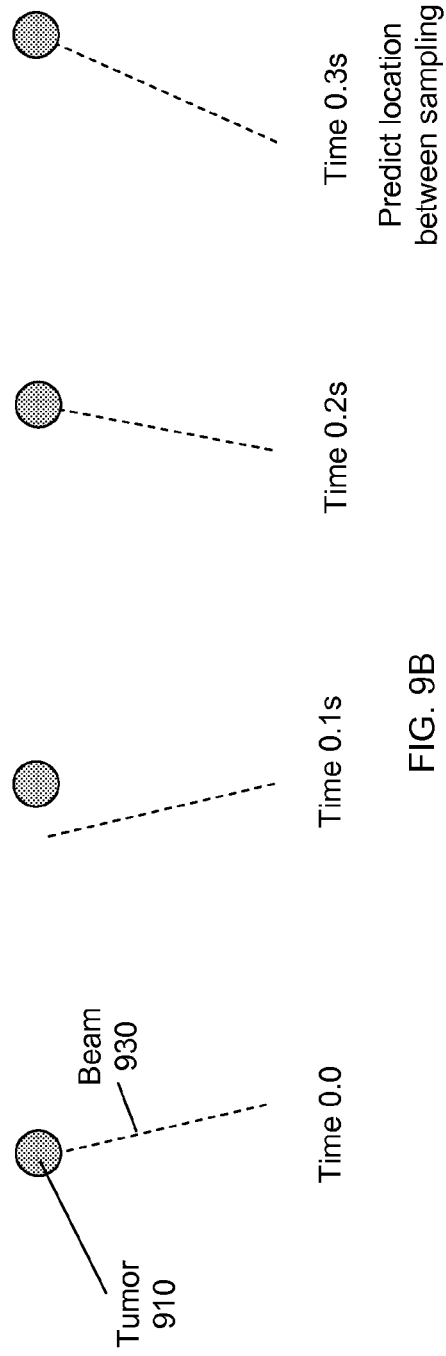
FIG. 9B shows an example of a prediction of a location of a tumor between sampling times where the prediction accounts for a delay between sampling and positioning of a beam according to embodiments of the present invention.

FIG. 9B shows an example of a prediction of a location of a tumor between sampling times where the prediction accounts for a delay between sampling and positioning of a beam according to embodiments of the present invention. At time 0.1, the beam 920 is still not focused on the tumor 910 since the system is still processing the new position information. However, for time 0.2 seconds, the system can use the position information at time 0.1 seconds to predict where the tumor will be at 0.2 seconds since that is the time the system knows corresponds to the delay. For example, once the system receives the sampled location information about the sensors at time 0.1 s, the system can calculate the predicted tumor location at 0.2 s (and just skip over any calculation of the tumor location at time 0.1 s since the beam cannot be positioned quick enough anyway). The delay for a particular system can be determined during a calibration process.

For time 0.3 s, the system can use the position information from times 0.1 s and 0.2 s, to calculate the tumor location at time 0.3 s. In one aspect, the tumor location of at time 0.3 s is fed into the beam positioning system prior to the time of 0.3 s. For example, assume that the delay to calculate the tumor location is 0.02 seconds and the delay to re-position the beam is 0.08 seconds, then the new tumor location is computed for 0.3 seconds (using the position information at times 0.1 s and 0.2 s) and is provided to the beam positioning system at 2.2 seconds, so that when the beam is re-positioned at time 0.3 seconds, the beam will approximately be at where the tumor is actually located at 0.3 seconds.

In some embodiments, a delta $\Delta$ (e.g. 0.1 s) can be added to the time of the prediction equation so that the position that is fed into the positioning system to position the beam is always 0.1 seconds greater than when the sensor locations were last sampled. For example, a velocity can be determined from the position of the tumor 910 at time 0.1 s and the location at time 0.0. Then assuming linear motion, this velocity can then be used in equation (position (x)=velocity* (time+$\Delta$)+initial position). Once further data points are obtained, more complex equations can be used with the time offset. Thus, in one embodiment, the computing system does not use the current time in the equations of motion, but uses the current time plus a time offset by $\Delta$.

Embodiments for handling the various delays can be combined. Thus, the beam's position can be updated more often than the sampling points, based on equations of motion derived from recent location measurements (i.e. sensor locations and subsequent calculation of tumor location). And, the equations of motion for the updates can use a time offset so that the position is the expected tumor location at the end of the re-positioning process. For example, if sampling of sensor locations is done every 0.2 s, a prediction engine can receive a new tumor location every 0.2 s; but the tumor location can be old by 0.02 seconds under the above example, where the delay of calculating the tumor location from sensor locations is 0.02. The prediction engine can predict the tumor location at a time of a current time 0.22 s (i.e. 0.02 seconds after the sampling time, in this example) plus a time offset of 0.08 s (the delay in the positioning mechanism) to obtain a predicted tumor location at 0.3 s. Assuming the prediction engine computes a predicted tumor location every 0.1 s (which can be more often than the sampled sensor locations are received), the prediction engine would compute the next tumor location (e.g. using the same equations of motion used for the calculation at time 0.22 s) at time 0.32 s with an offset of 0.08 s to provide a predicted tumor location at 0.4 s.

Besides using a fixed offset $\Delta$ for computing the next position, the time-dependent functions to predict tumor position (and possibly undesired tissue position) can be used in combination with the response of the beam assembly positioning as a function of time. The response time to position the beam may change over time, e.g., the response time may be longer when the tissue is moving faster and the beam assembly must move faster to keep up, thereby resulting in more time lag. As another example, different delays can be encountered depending on the last position of the beam and what the new commands are. Such different delays can be due to different total distances that the beam assembly needs to be moved. The beam assembly can be made to move faster when the distance to be moved is more, but in general, the movement speed of the beam assembly should correlate to the time step for the new position (i.e. related to the average velocity of the tissue and/or beam over the time period) so that the beam assembly would be focused on the tissue during the movement of the beam.

The response time can be measured for each new set of input commands for changing the position of the radiation beam, thus a function G of the response time that approximates these data points can be determined (e.g., by computing coefficients of basis functions that minimize a cost function). The cost function can include contributions from a difference in the time-response function G from the measured response time. The function G could also be determined from the values of the time-dependent function for the tissue. For example, the response time could be estimated from the acceleration of the tissue, or from higher order terms (such as the change in the acceleration). The time-response function G can be pre-computed during a calibration process, and may be updated during treatment.

C. Determining Beam Position from Tissue Position

Using the embodiments described above, one can calculate the position of tumor and/or healthy tissue at a given time. A number of different positions can be obtained for each time. The different positions can include multiple positions on a surface of a tumor, positions of multiple tumors, and multiple positions for various healthy tissues. All of these positions can be used to determine an optimal beam position, as well as any other beam properties, such as beam intensity, beam width, etc.

The optimal beam can be computed by optimizing a cost function. For example, the optimal position can minimize the cost function, which can have contributions due to tumor and healthy tissue. The cost function can decrease when there is more overlap of the beam with the tumor (i.e. the beam is hitting the tumor), but increase if there is more overlap with healthy tissue (e.g. a penalty is paid for hitting healthy tissue). The cost function can be tailored such that the penalty for hitting healthy tissue is high (and also may vary depending on the exact healthy tissue that would be hit, such as the heart) relative to the benefit (i.e. reduction in the cost function) for more overlap for the diseased tissue.

D. Method of Predicting Location of Tissue

Figure 10:
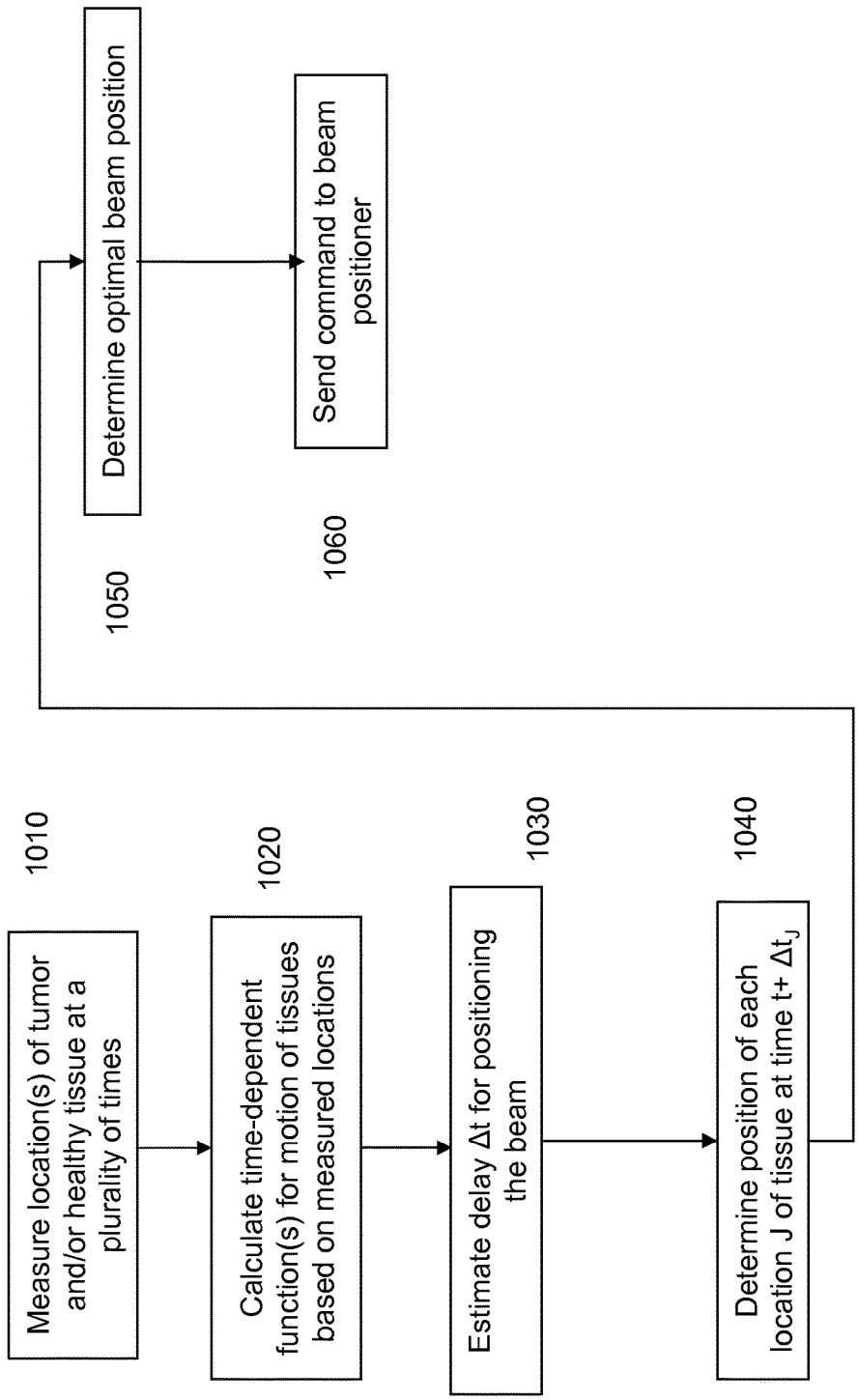
FIG. 10 is a flowchart illustrating a method 1000 for tracking motion of tissue and determining an optimal beam position based on the motion according to embodiments of the present invention.

FIG. 10 is a flowchart illustrating a method 1000 for tracking motion of tissue and determining an optimal beam position based on the motion according to embodiments of the present invention. Method 1000 uses time-dependent functions to predict motion of tissue and an estimate of delay in the system to account for various system errors.

In step 1010, one or more locations of tumor and/or healthy tissue are measured at a plurality of times. The measurement may be made as described above, for example, combining a less precise method during treatment (e.g., using locations of fiducials) with a model for mapping the less precise measurements to more precise measurements. The less precise measurement could be internal measurement, e.g., using standard x-ray, or external measurement, e.g., using wireless sensors (as described above) or imaging techniques. The times may be the N most recent measurements, or all of the measurements within a prescribed time.

In step 1020, time-dependent function(s) for motion of the tissues are calculated based on the measured locations. Each different tissue can have its own time-dependent function, and even multiple locations on each tissue can have a separate time-dependent function. Each location can be broken up into separate dimensions (e.g. Cartesian coordinates, spherical, cylindrical, and so on), and thus each location have three different time-dependent functions, one for each dimension.

The time-dependent function can be determined in a variety of ways. For example, one may use a set of basis functions (e.g. polynomials in time t), and determine the coefficients that best approximate the motion defined by the measurements from step 1010. Thus, the time-dependent functions could be of the form $a+bt+ct^2$, with a being the initial offset, b being velocity, and c being an acceleration term (e.g. proportional to acceleration). Higher order polynomials can be used, as well as other basis functions. The coefficients of the basis functions can be determined by optimizing a cost function, e.g., mean square difference or worst square difference between the time-dependent function and the measured data points from step 1010. Non-linear variables can also exist within the basis functions, but such inclusion can make their calculation more difficult.

Accordingly, a time-dependent function can have the generic form of $X_{I,J}(t)=F(C,t)$, where X is a matrix with one dimension (e.g. I) being three and the other dimension (e.g. J) being the number of locations whose motion is being modeled, and where $C_{I,J,M}$ is a $3^{rd}$-rank tensor (or simply an array with three dimensions) of the coefficients that are determined via the optimization step. The index M can run over the number of variables defining the time-dependent function for the particular coordinate I of location J of a tissue. Then, C can be determined by optimizing a cost function $E(C,t,Y)$, where Y is the measured data points from step 1010.

In one embodiment, E can equal $\Sigma(Y-F)^2$, where the sum is over each time point, number of coordinates, and number of locations of tissue being tracked. Note that each time-dependent function can be treated as a separate function. Alternatively, the motion for different coordinates locations can be dependent on each other, e.g., the locations on a surface of a tumor would have some correlation with each other. Additionally, the variables for the location(s) of different tissue can be calculated with different accuracy. This may be achieved using different weightings in the cost function E. For example, the sum of the least square errors for a particular location(s) of an object (tissue) can be multiplied by a larger factor in order to give more importance to obtaining accurate values of C for the object.

The function F can be re-calculated for each new data point, or every Nth data point, where N is grater than one. The calculation of F can be independent from how often a new command is given to the apparatus for positioning the beam. For example, F can be re-calculated every 0.5 seconds, but a new command can be sent to the beam positioner (also called a movement mechanism) every 0.1 seconds. Thus, the last F can be re-used to determine new positions for the beam.

In step 1030, the delay $\Delta t$ for positioning the beam is estimated. In one embodiment, $\Delta t$ could be chosen as a fixed value. For example, the system could assume that from the time of computing the locations (which could include or not include determining the time-dependent function F), including the time to compute the optimal beam position, until the beam is positioned at its new designated position (i.e. as designated by the commands given to the positioner) is a constant. In another embodiment, the value of $\Delta t$ can be different. For example, if the tissue is moving faster, it will take longer for the beam assembly to move into the correct position. Thus, $\Delta t$ can be larger. Note that if $\Delta t$ was large enough, the beam may not reach its final designated location by the time a new command is given to the positioner.

For a variable delay $\Delta t$, the time may be estimated based on the values of C. For example, the maximum coefficient for the velocity or acceleration can be used to determine $\Delta t$, as that acceleration can dictate how long it will take to position the beam. In yet another embodiment, the value of $\Delta t$ can vary for each location being tracked.

In other embodiments, $\Delta t$ can be determined from any combination of distance traveled for last time step, error of predicted position from actual position of tissue, and a beam error of actual trajectory of the beam from an optimal trajectory of the beam. Using the feedback of the beam error can allow for machine learning, e.g., via optimization algorithms to determine better input commands into a beam assembly for moving the beam. The actual trajectory can be computed, e.g., as described in section V above.

In step 1040, the position of each location J of tissue is determined at time $t+\Delta t_J$, where t is the current time. The result is that the location of the tissue is computed for a future time. Since the beam is expected to take $\Delta t_J$ to move to the position at $t+\Delta t_J$, the beam is expected to move along a similar trajectory that that the tissue is moving. Thus, the error is reduced compared to using the position of the tissue at the current time.

In step 1050, the optimal beam position can be determined, e.g., as described above. For instance, a cost function that uses locations of tumor tissue and healthy tissue can be used to find a beam trajectory that reduces risk to vital organs while providing radiation to the tumor. In some cases, the radiation beam could be turned off if the certain criteria cannot be met (e.g., the cost function is above a certain value, which can indicate that healthy organs would be damaged). Once an optimal beam position is determined commands for a beam positioner can be determined. In one aspect, the optimal beam position can be a command.

In step 1060, the command for the new position is sent to the beam positioner. The commands may be analog or digital signals. The beam positioner may be a stepping motor. In one embodiment, the commands may be high level commands that specify a position of the beam assembly or a particular trajectory. The beam positioner can include a processor that receives the high level position commands and determines the specific signals to send to actuators for moving the radiation beam.

Regarding the calculation of the time-dependent functions, some embodiments can use certain information to determine what kind of motion is occurring. For example, which sensors are moving can be used to predict how the patient's body is moving. If the sensors on the patient's torso are moving rotationally, then the person's whole body is likely turning. If the tumor is located within the torso, the motion of the tumor is likely around an axis within the patient's body. Thus, rotating motion can be assumed, and the corresponding equations can be used. Certain criteria can be used to classify the type of motion, and then use equations corresponding to that type of motion. Other implementations can use a single more general equation for multiple types of motion.

As another example, the sensors could identify that the patient is moving his/her arm or leg. If the tumor is within the arm or leg, then the motion can be constrained by knowledge of the patient's body, such as length of the arm or leg and knowledge that only certain types of motions are possible (e.g. hinge-like motion for the elbow or knee). Thus, the knowledge of the type of motion and the physical constraints of what motions are possible can be used to accurately predict where a tumor may be.

In one embodiment, the beam can be turned off if the movement of the patient is measured (via the sensors on the patient) to be faster than a threshold value, and/or erratic enough that a prediction is deemed not to be accurate within a threshold. The threshold may be determined based on how fast the system can determine the tumor location and change the beam trajectory, e.g., a latency of the system. This threshold for the rate of acceptable movement can be determined during a calibration procedure, e.g., using a dummy instead of a real patient.

VII. Determining Trajectory of Optimal Beam Position

In the last section, the position of the tumor as a function of time was determined. Based on this predicted motion, an optimal beam position was determined for a particular time. In the embodiments of this section, the position of the tumor as a function of time need not be determined. Instead, a beam trajectory can be determined as a time-dependent function of beam position (e.g., 3-dimensional location and 2-dimensional angle). The beam trajectory can be determined to minimize an error between an actual beam position (e.g., as measured) and an optimal beam position at a set of times. The optimal beam position at a particular instant in time can be determined based on a determination of a position of a tumor and/or healthy tissue at the particular instant in time (e.g. via a measurement made at that instant in time).

A. Method Using Feedback Error

Figure 11:
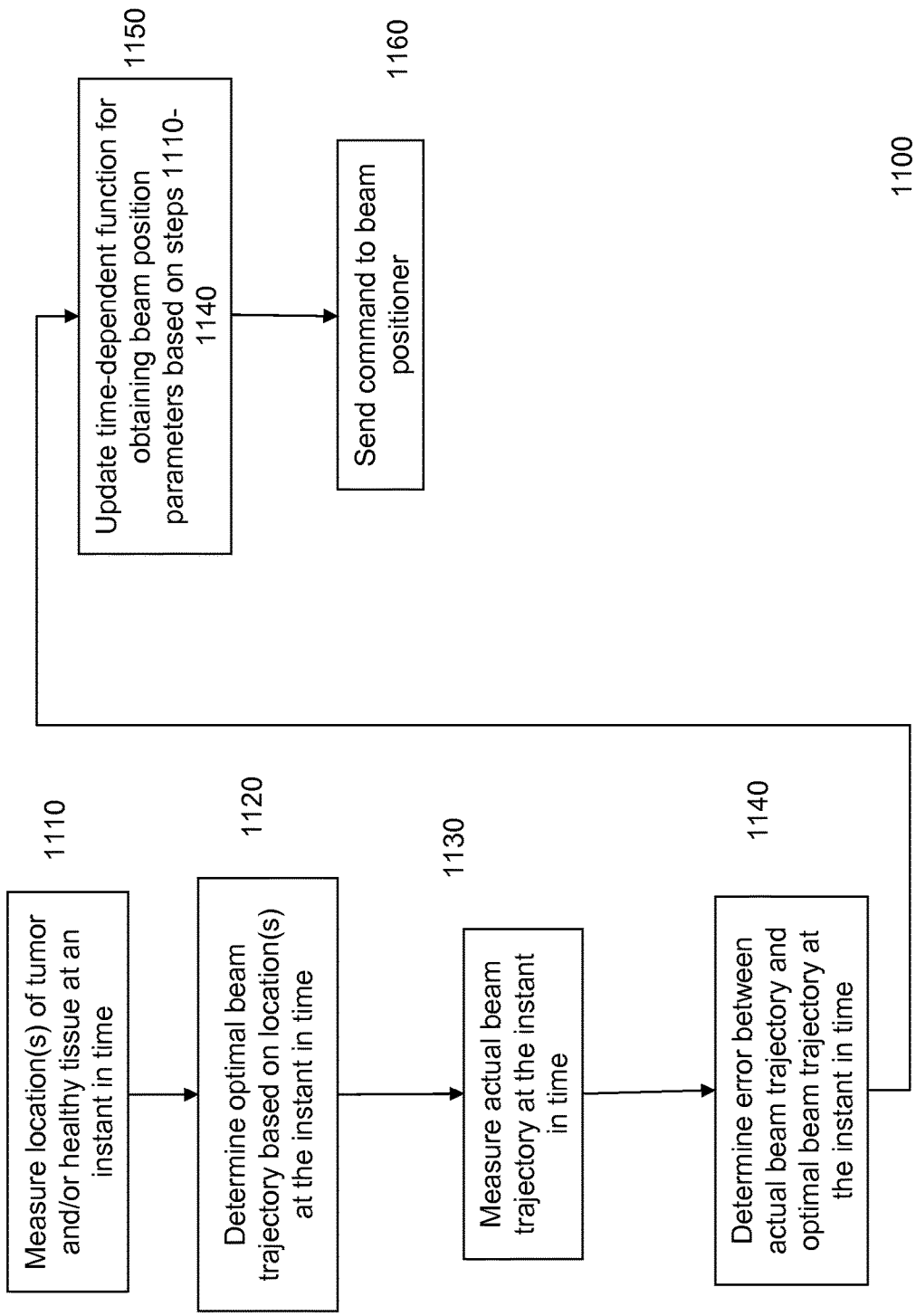
FIG. 11 is a flowchart illustrating a method 1100 for determining an optimal beam position based on feedback error according to embodiments of the present invention.

FIG. 11 is a flowchart illustrating a method 1100 for determining an optimal beam trajectory based on feedback error according to embodiments of the present invention. Method 1100 uses time-dependent functions that account for the motion of the tissue. The time-dependent functions could be used to predict the motion of the tissue, or used to predict the change over time of an optimal beam trajectory or inputs to a beam positioner.

In step 1110, location(s) of tumor and/or healthy tissue is measured at an instant in time. The location can be performed using methods described herein, e.g., using a mapping model obtained from pre-treatment scans. The locations of the tissue could also be obtained directly with fiducials attached to the tissue. Any suitable method for measuring the location may be used.

In step 1120, an optimal beam trajectory can be determined based on the location(s) of the tissue(s) at the instant in time. For a given location of tumor and/or healthy tissue, an optimal trajectory can be chosen. The term optimal as used herein does not require the best trajectory possible, but a value that is determined optimal within a specific criteria (e.g., a cost function is below a certain value). Accordingly, the optimal trajectory could hit some healthy tissue, but the amount would be within specific parameters.

In step 1130, the actual beam trajectory is measured at the instant in time. The actual beam trajectory can be measured as described herein. For example, the radiation beam may hit detectors, which can identify a particular location of the disturbance of the detectors. As another example, beam sensors (e.g. as described in FIG. 7) can be used to determine the beam trajectory at the particular instant in time.

In step 1140, an error between the actual beam trajectory and the optimal beam trajectory at the instant in time can then be determined. The error can result from various factors as described herein. An error can be computed for each degree of freedom of the beam trajectory, e.g., three spatial coordinates and two angular coordinates. The measurements of the actual beam trajectory can be determined on a continuous basis, and stored with a time stamp. Once the tumor location is determined, the time $t_0$ can also be stored, so that the corresponding optimal beam trajectory at time $t_0$ can be compared to the actual beam trajectory at time $t_0$. In one embodiment, the error for different degrees of freedom can be weighted differently, e.g., the angular degrees of freedom can be weighted higher as they may have more of an impact on the change of the cost function for a beam trajectory.

In step 1150, a time-dependent function for obtaining beam trajectory parameters is updated based on any one or more of the values obtained in steps 1110-1140. In various embodiments, the time-dependent functions can specify the motion of the tissue, the change in the optimal beam trajectory over time, and the change in input commands to a beam positioner. The update can include changing a time offset for determining the next input command (e.g. providing a command for a future point in time to account for delays in the system) or parameters that affect the actual next input command (which could be any parameter for any of the time-dependent functions).

In step 1160, one or more commands are sent to a beam positioner. The input commands provided at a time $t_0$ could be for a different beam trajectory than the optimal beam trajectory at time $t_0$. For example, the input could be for a greater position than the optimal position at time $t_0$, but due to time lag $\Delta$, the actual beam position at time $t_0+\Delta$ will be or approximately be the optimal beam position for time $t_0+\Delta$. Thus, the input commands can be determined to reduce the error between the actual and optimal beam trajectory for a set of measurements at different times.

In some embodiments, the beam assembly can have a continuous motion as opposed to discrete movements to new positions. For example, commands can provide parameters for equations of motion of the beam assembly, as described herein. Such parameters can include velocity and acceleration, or other variables for any suitable time-dependent function. The positioning system can then move the beam assembly according to those equations, whose parameters are based on the positions of the sensors. Such embodiments can take in account present or past beam assembly velocity and/or present or past beam assembly acceleration. For example, changes in velocity or acceleration to new values can have different delay based on what the current or previous values were. A time-response function G to predict delays in positioning the radiation beam can be computed as described above. This time-response function can be calibrated and recorded. The time-response function G can then be used to estimate the ideal beam position commands (e.g. by determining the proper time offset at a given instant in time) or simply changing the variables to account for any delays.

B. Updating Time-Dependent Function for Beam Position Parameters

The feedback of the errors in the actual beam position and the optimal beam position can be used to various ways to update the time-dependent functions of the beam position parameters. For example, a time-dependent function can be determined for the optimal beam trajectory, and the beam error from step 1140 can be used to determine a time offset (e.g. due to lag), in a similar manner as explained for method 1000. As another example, a time-dependent function can be determined for the beam position parameters. This time-dependent function would typically not be the same as for the optimal beam trajectory, and thus can incorporate any lag in the system into the function itself without using a time offset.

Update $\Delta t$

The time-dependent function for the optimal beam trajectory can be calculated from the optimal beam position determines at a plurality of times. Each position of the beam can have a separate time-dependent function. As the beam can have two angular degrees of freedom, along with the three-dimensional spatial coordinates, five time-dependent functions could be used. The functions can have an assumed functional form (basis functions), such as polynomial, which could be of the form $a+bt+ct^2$ or of higher order, as mentioned above. But, other basis functions suitable for periodic motion can be used. A cost function, such as least square error, can be used to determine the variables defining the functions.

Even if the time-dependent function was of such precision to exactly predict the next optimal beam position, there can still be an error due to the imprecision of the positioning mechanism for the beam, or any time lags in the calculations and the positioning. Thus, an beam error determined in step 1140 can be non-zero. To account for such errors, a time-offset $\Delta t$ can be used in a similar manner as described above. A single time-offset $\Delta t$ can be used for all of the time-dependent functions, or the time-offset $\Delta t$ can vary between the different time-dependent functions. Thus, each degree of freedom can have its own value for $\Delta t$. The value of $\Delta t$ can be determined in a similar manner as mentioned above. For example, $\Delta t$ can be determined from the beam error, the variables of the time-dependent functions (e.g. a coefficient corresponding to velocity and/or acceleration), and the change in position of the tissue being tracked between sampling times.

In one embodiment, the beam error can be used as feedback to increase or decrease the value of $\Delta t$. For example, if the error is a result of an overshoot (i.e. the beam was moved past the optimal location), the value of $\Delta t$ can be reduced for the next determination of the beam position. The exact amount of reduction can be determined via an optimization algorithm that uses previous errors and the corresponding $\Delta t$ values. For an undershoot, the value of $\Delta t$ can be increased. If the error is zero or almost zero (e.g. within a threshold of zero), then the value of $\Delta t$ can remain unchanged. As a beam error can be computed for each degree of freedom of the beam position, a different value of $\Delta t$ and change to $\Delta t$ can be used for respective time-dependent functions corresponding to the different degrees of freedom. As the value of $\Delta t$ is being updated, the time-dependent function of the optimal trajectory can be re-calculated for each new data point of the optimal beam position.

Update Coefficients for Time-Dependent Function of Beam Parameters

In another embodiment, a time-dependent function(s) of the optimal trajectory is not calculated, but instead a time-dependent function(s) of the input positions (commands) into the beam assembly for positioning the beam. In this manner, the time-dependent function is not necessarily related to any particular movement, but can be computed as the function that minimizes the beam error. However, input values for one or more previous positions of the tissue may be used.

The initial values for the variables of the time-dependent functions can be computed in a similar manner as for the optimal beam trajectory. For example, a function approximating the data points of the optimal beam trajectory can be computed. In another embodiment, the error at a particular instant in time can be paired with a particular input to the beam assembly, thereby providing an error in the initial values for the variables. Combining the error with the actual input values (e.g., input position), one can determine an estimated value for the optimal input values. The time-dependent functions for the input positions can then be computed in a similar manner as any of the functions mentioned above. One can also compute the time-dependent function as delta value for how the beam assembly should move based on a most recent value for the beam position. This delta value in the change of the function value can itself vary over time, e.g., as computed based on an optimization of a cost function using previous errors.

Once the variables of the time-dependent function(s) for the input positions are determined, the variables themselves can be updated based on the measured beam error. The variables can be updated in various ways. For example, the variables can be updated as each new error point is received. The direction of change can be computed in a similar manner as for $\Delta t$. As another example, the variables can be updated by combining the error with the actual input values, as is described above.

In practice, the combining the error with the actual input values can involve optimization algorithms, such as conjugate gradient (with the error being the gradient) or quasi-Newton methods, or other types of machine learning. The basis functions for the time-dependent functions can include neural networks and delta functions (e.g., simply vector values at different instances in time), as well as others mentioned above. The new values for the variables defining the time-dependent function(s) would then be chosen so as to minimize (or at least reduce) the measured beam error. The cost function for the optimization would involve the beam error(s) (e.g., one for each degree of freedon), and could simply be a sum of the beam errors at the times being used, or some other function. The various beam errors could be given different weightings, e.g., if reducing the error for angle is more important than a spatial placement of the beam assembly itself, or vice versa. The use of a value of $\Delta t$ can also be combined with this method.

VIII. Transforming Pre-Treatment Image

As mentioned above, a digital pre-treatment body image of a patient can be created using various techniques (such as CT, MRI, and ultrasound). The pre-treatment body image can include a characterization of the spatial characteristics of one or more first components (e.g. tumor and/or healthy tissue) of the body anatomy relative to one or more markers. As detailed above, the markers may be natural features of the patient's body (e.g., particular locations on bones, a nose, belly button) or artificial markers that are added to the patient's body (e.g. on the surface or internally). The digital pre-treatment body image can be created using one imaging technique (e.g. the markers also are imaged with the same technique as the tumor tissue) and two techniques are used (e.g. the marker locations are determined with optical or radio frequency signals).

The pre-treatment body image may not be consistent with a treatment coordinate system. An embodiment can determine whether the pre-treatment body image is consistent with the treatment coordinate system. If the pre-treatment body image is not consistent with a treatment coordinate system, the pre-treatment body image can be mapped into a corrected pre-treatment body image that has a coordinate system that is consistent with the treatment coordinate system. The treatment coordinate system can enable the location and/or orientation of the one or more first components of the body anatomy with respect to a location and/or a pointing angle of a radiation treatment apparatus (e.g. a beam trajectory). For example, the pre-treatment body image can be scaled to the resolution (e.g. by altering the number of pixels in the image) of the detectors used during treatment to detect the sensors and position the beam, thereby allowing a unified coordinate system. This mapping can be performed before treatment begins. If the pre-treatment body image is consistent with a treatment coordinate system, then no correction may be necessary, and the corrected pre-treatment body image would be the pre-treatment body image.

During treatment, a digital treatment body image can be created. The digital treatment body image is consistent with the treatment coordinate system. The sensors can be located as key features on the treatment body image in the treatment coordinate system. The positions of the sensors can be obtained in various ways (such as x-rays, MRI, optical imaging, or ultrasound). For example, an x-ray scan can provide an image with identifiable locations of bones, fiducials, or other sensors that provide a signal to detectors. As another example, optical imaging using video or still pictures (or other wireless communication) can be used to detect natural body features or artificially added sensors. Any of these and other suitable techniques can provide a digital treatment body image. In one embodiment, the pre-treatment body image is created in a different apparatus than where the treatment body image is created.

A best-fit process (e.g. using optimization techniques described herein) can be used to map information (e.g. positions of tissue and sensors) from the corrected pre-treatment body image to the treatment body image to create an enhanced treatment body image, which is consistent with the treatment coordinate system. The best-fit mapping can determine a position offset and/or a rotation offset to apply to the entire corrected pre-treatment body image, to respective sections of the corrected pre-treatment body image (e.g., if the body has a twist or is bent), or different offsets for different components (e.g. sensors and tissue) to re-position the corrected pre-treatment body image. For example, the offsets can minimize a position difference as measured in the treatment coordinate system between a set of one or more common features (e.g. sensors and tumor tissue) in the re-positioned corrected pre-treatment body image and the same set of common features in the treatment body image. The optimization can be constrained so that the offsets reflect possible distances between the two different features (e.g., a hip joint may only have a certain range of possible distances from a nearby tumor).

The enhanced treatment body image can be used to identify a feature (e.g. a sensor) in the image and to determine a desired radiation target (e.g. the tumor tissue) within the treatment coordinate system. Identified features can also be used to determine undesirable radiation targets (e.g. healthy tissue) that is not to be radiated. A control processor can determine a pointing location and/or pointing angle of the radiation treatment apparatus (e.g. a beam assembly) that will cause a radiation beam to hit the desired radiation target (e.g. beam has an optimal beam trajectory). Commands can be provided to the radiation treatment apparatus to cause the radiation treatment apparatus to move to the pointing location and/or pointing angle and deliver a radiation dose.

The treatment body image may be body points identified by markers (sensors) placed on the body. In one embodiment, the markers can be located with wireless position finding techniques, and the treatment apparatus can include detectors to locate the markers in the treatment coordinate system. In another embodiment, the markers can be located with video or still camera imaging techniques, and the treatment apparatus can includes video or still cameras to locate the markers in the treatment coordinate system. The placement of the markers on the body during treatment imaging can be the same, or within a tolerance, as the placement of pre-treatment markers placed on the body during pre-treatment imaging. The treatment markers and the pre-treatment markers can have the same image properties for pre-treatment imaging and treatment imaging. The markers can have an image property that provides enhanced marker location during treatment imaging (e.g. relative to other features in the image) and the pre-treatment markers have an image property that provides enhanced marker location during pre-treatment imaging. In yet another embodiment, the markers (e.g. internal markers) can be located with x-ray techniques, and the treatment apparatus can include x-ray apparatus to locate the markers in the treatment coordinate system.

The treatment apparatus used to locate the markers in the treatment coordinate system can be calibrated prior to treatment by capturing an estimated position in the treatment coordinate system of a test marker of known location in the treatment coordinate system and applying a correction factor to the estimated position so that it correctly maps to the known position in the treatment coordinate system.

In one embodiment, the enhanced treatment body image is used to: (i) enhance one or more image properties and/or one or more location estimates of a first set of image features (e.g. healthy tissue) in the treatment image, or (ii) add one or more image features (e.g. the diseased tissue) in a second set of image features to the treatment body image, where the second set of image features are identifiable in the re-positioned corrected pre-treatment image and are not identifiable in the treatment image. In one embodiment, the one or more first set of features can include image features resulting from markers placed on or near the body. In another embodiment, the one or more first set of features can include body features or anatomy elements identified by a body anatomy identification algorithm applied to the image. The one or more second set of features can include body features or anatomy elements.

Mapping the pre-treatment body image the treatment coordinate system can be accomplished by calibrating the apparatus used to create the pre-treatment body image so that an absolute measure of dimensions is obtainable from the pre-treatment body image information. The mapping to a corrected pre-treatment body image can then be based on the known absolute dimension information available in the pre-treatment body image. Mapping the pre-treatment body image into the treatment coordinate system can be accomplished by inserting calibration markers of known absolute geometry placed on or near the body during the pre-treatment imaging process. The known absolute geometry of the calibration markers can be used to adjust the pre-treatment body image so that the corrected geometry of the calibration markers in the corrected pre-treatment body image is consistent with their known absolute geometries.

In one implementation, the location and/or a pointing angle of a radiation treatment apparatus can be determined by a pre-treatment calibration procedure wherein a position and/or pointing angle command is provided to the radiation treatment apparatus. The resulting position and/or pointing angle of a radiation beam can be measured with respect to the treatment coordinate system. The process may be repeated until a characterization of multiple position and/or pointing angle commands and the resulting position and/or pointing angle measured in the treatment coordinate system is sufficient to achieve the required accuracy during treatment. In another implementation, the location and/or a pointing angle of a radiation treatment apparatus can also determined by placing markers on the treatment apparatus elements that direct a radiation beam, locating the position of the markers in the treatment coordinate system, and applying a mapping of the location of the markers in the coordinate system to the location and/or a pointing angle of a radiation treatment apparatus in the treatment coordinate system.

Determining a pointing location and/or pointing angle of the radiation treatment apparatus that will cause a radiation beam to hit the desired radiation target can include using one or more past positions of the desired radiation target and an estimate of motion dynamics of the desired radiation target to improve the accuracy of the pointing location and/or pointing angle with respect to the actual real time location of the desired radiation target, e.g., as described above. The enhanced treatment body image may further utilized to identify one or more undesired radiation features in the image and use the one or more undesired image features to determine one or more undesired radiation targets within the treatment coordinate system. Determining a pointing location and/or pointing angle of the radiation treatment apparatus may not only be based on the location of the desired present state radiation target, but also based on the one or more undesired present state radiation targets that are desired to be avoided when determining the present pointing location and/or pointing angle of the radiation treatment apparatus in the treatment coordinate system. The desired treatment path can include a series of future pointing locations and/or pointing angles that will result in more exposure to the desired radiation target than is delivered to other body features including the one or more undesired radiation targets. As time progresses, each of the future pointing locations and/or pointing angles may be used to assist in deriving a present state pointing location and/or pointing angle.

In one embodiment, the best-fit process to create an enhanced treatment body image can include identifying a first set of body model reference features in the treatment image, determining a body-model orientation based on the relative position of the body-model reference features in the treatment body image, utilizing the body-model orientation to obtain a body-model enhanced version of the corrected pre-treatment body image, and then applying the position offset and a rotation offset to the body-model enhanced corrected pre-treatment body image to create the re-positioned corrected pre-treatment body image. The body model may be a mathematical model that determines an enhanced location estimate for a second set of body features based on the relative position of the body-model reference features in the treatment body image. The second set of body features may be features that are not available, or have poor quality or resolution in the treatment image.

In another embodiment, the best-fit process to create an enhanced treatment body image can include identifying a first set of body model reference features in the treatment image, identifying from a plurality of secondary pre-treatment images a subset of two or more closest fit images wherein the relative position of the body-model reference features in the closest fit secondary pre-treatment images is close to the relative position of the body-model reference features in the treatment image, applying an interpolation algorithm to two or more secondary pre-treatment images to create an improved interpolated closest fit pre-treatment body image, and then applying the position offset and a rotation offset to the improved interpolated closest fit corrected pre-treatment body image to create the re-positioned corrected pre-treatment body image.

IX. Computer System

Figure 12:
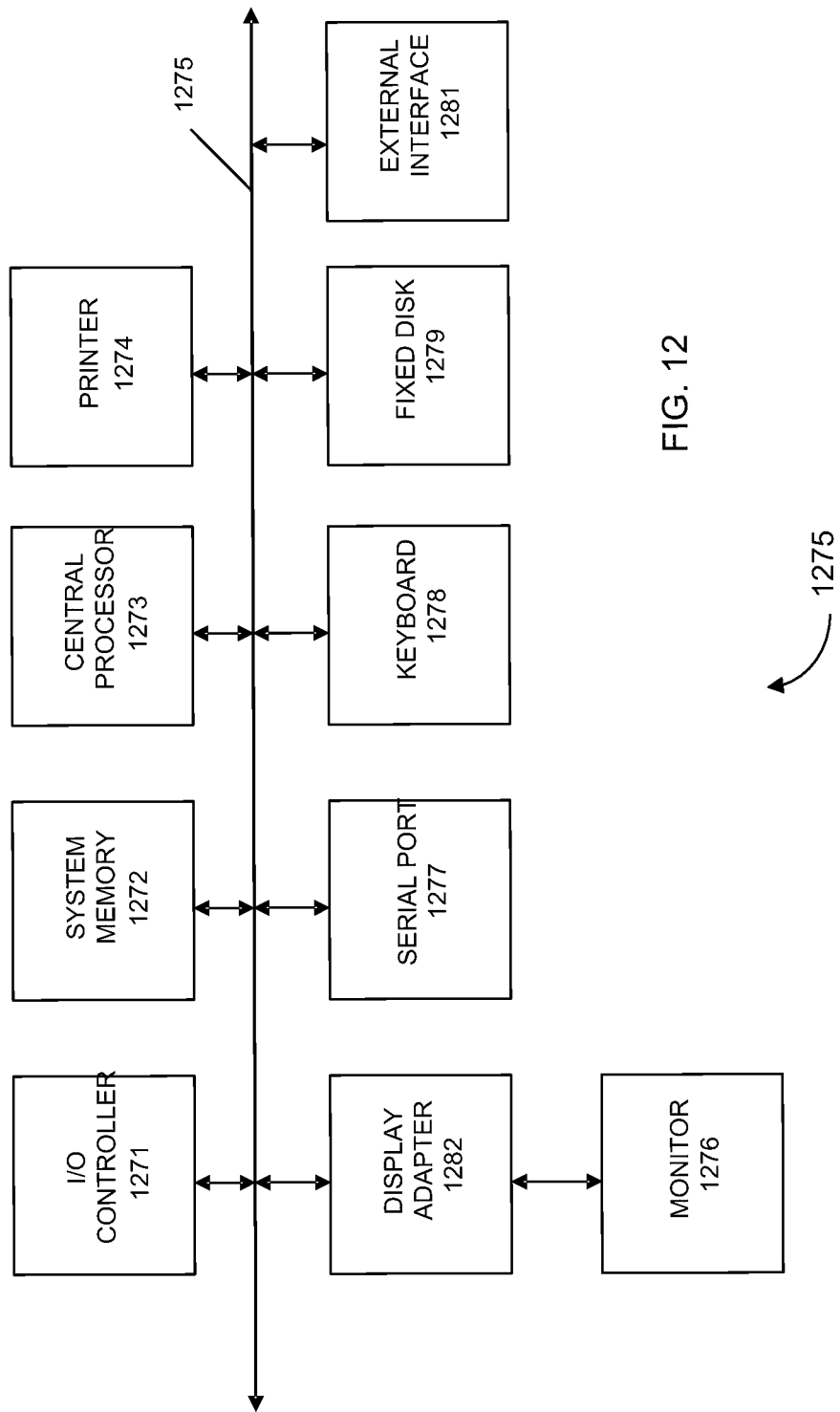
FIG. 12 shows a block diagram of an example computer system 1200 usable with system and methods according to embodiments of the present invention.

Any of the computer systems mentioned herein may utilize any suitable number of subsystems. Examples of such subsystems are shown in FIG. 12 in computer apparatus 1200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 1275. Additional subsystems such as a printer 1274, keyboard 1278, fixed disk 1279, monitor 1276, which is coupled to display adapter 1282, and others are shown. Peripherals and input/output (I/O) devices, which couple to I/O controller 1271, can be connected to the computer system by any number of means known in the art, such as serial port 1277. For example, serial port 1277 or external interface 1281 can be used to connect computer system 1200 to a wide area network such as the Internet, a mouse input device, or a scanner. The interconnection via system bus 1275 allows the central processor 1273 to communicate with each subsystem and to control the execution of instructions from system memory 1272 or the fixed disk 1279, as well as the exchange of information between subsystems. The system memory 1272 and/or the fixed disk 1279 may embody a computer readable medium. Any of the values mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

What is claimed is:

1. A system for directing a radiation beam to a location of a diseased tissue region of a patient, the system comprising:
   a beam assembly configured to emit a directed radiation beam;
   one or more detectors configured to receive a signal from at least one sensor, the signal usable to detect motion of the patient; and
   one or more processors in communication with the beam assembly and the one or more detectors, the one or more processors configured to
      based at least in part on the signal usable to detect motion of the patient received by the one or more detectors, determine one or more parameters for a first time-dependent predictive motion model for a diseased tissue region, use the first motion model to calculate a future trajectory for the radiation beam to target one or more predicted future locations of the diseased tissue region different than a last-known location of the diseased tissue region, and adjust the beam assembly such that the radiation beam follows the calculated trajectory.

2. The system of claim 1, wherein the one or more processors are further configured to:

obtain a digital pre-treatment body image; and map the pre-treatment body image into a treatment coordinate system.

3. The system of claim 2, wherein the digital pre-treatment body image is obtained from a different system.

4. The system of claim 1, wherein the one or more processors are further configured to, based at least in part on the signal usable to detect motion of the patient received by the one or more detectors, determine one or more parameters for a second time-dependent predictive motion model for a plurality of locations of healthy tissue near the diseased tissue region, and wherein configured to use the first motion model to calculate a future trajectory further comprises configured to use the second motion model to adjust the future trajectory to reduce a radiation exposure at one or more predicted future locations of healthy tissue near the diseased tissue region.

5. The system of claim 1, wherein the at least one sensor comprises a sensor that is configured for placement internal to the patient.

6. The system of claim 1, wherein the at least one sensor comprises an external marker configured for placement at a surface of a body of the patient.

7. The system of claim 1, wherein the at least one sensor is configured for placement at a known position relative to a marker with a known location relative to the diseased tissue region, the one or more processors further configured to account for relative positioning between the at least one sensor and the marker in the first time-dependent predictive motion model.

8. The system of claim 1, further comprising a beam sensor, the one or more detectors including at least one detector configured to receive a beam sensor signal from the beam sensor, the one or more processors configured to calculate a position of the beam assembly from the beam sensor signal.

9. The system of claim 1, wherein the one or more processors are further configured to, based on a signal usable to detect motion of the patient faster than a threshold, shut off the radiation beam.

10. The system of claim 1, wherein the one or more processors are further configured to adjust the beam assembly with predictive adjustment commands that account for a delay in positioning the beam assembly relative to a timing of the commands in order to follow the calculated trajectory.

11. The system of claim 1, wherein the one or more sensors are wireless.

* * * * *